(12) United States Patent
Schneider et al.

(10) Patent No.: US 9,682,079 B2
(45) Date of Patent: Jun. 20, 2017

(54) COMPOSITION FOR TREATMENT OF PATHOGENS THAT ARE RESISTANT TO TETRACYCLINES

(71) Applicant: BIOVERSYS AG, Basel (CH)

(72) Inventors: Peter Schneider, Bottmingen (CH); Rainer Riedl, Wilen bei Wollerau (CH); Marcel Tigges, Reinach (CH); Marc Gitzinger, Eiken (CH); Michel Pieren, Binningen (CH); Assaf Levi, Basel (CH); Mark Sephton, Cambridge (GB); Birgit Schellhorn, Well am Rhen (DE); Patrik Zueger, Adliswil (CH); Michael Brand, Staufen (CH); Daniel Gygax, Himmelried (CH); Peter Spies, Zwingen (CH)

(73) Assignee: BIOVERSYS AG (CH)

( * ) Notice: Subject to any disclaimer, the term of this patent is extended or adjusted under 35 U.S.C. 154(b) by 0 days.

(21) Appl. No.: 14/765,446

(22) PCT Filed: Feb. 3, 2014

(86) PCT No.: PCT/EP2014/052012
§ 371 (c)(1),
(2) Date: Aug. 3, 2015

(87) PCT Pub. No.: WO2014/118361
PCT Pub. Date: Aug. 7, 2014

(65) Prior Publication Data
US 2015/0359791 A1    Dec. 17, 2015

(30) Foreign Application Priority Data
Feb. 4, 2013    (EP) .................................... 13153813

(51) Int. Cl.
| | | |
|---|---|---|
| A61K 31/495 | (2006.01) |
| A61K 31/16 | (2006.01) |
| A61K 31/165 | (2006.01) |
| A61K 31/166 | (2006.01) |
| A61K 31/167 | (2006.01) |
| A61K 31/4965 | (2006.01) |
| C07C 233/18 | (2006.01) |
| C07C 233/25 | (2006.01) |
| C07C 233/29 | (2006.01) |
| C07C 233/73 | (2006.01) |
| C07C 235/40 | (2006.01) |
| C07C 235/60 | (2006.01) |
| C07C 235/82 | (2006.01) |
| C07D 285/135 | (2006.01) |
| C07D 295/192 | (2006.01) |
| A61K 31/433 | (2006.01) |
| A61K 31/65 | (2006.01) |
| C07C 235/66 | (2006.01) |
| C07C 235/84 | (2006.01) |

(52) U.S. Cl.
CPC ............ *A61K 31/495* (2013.01); *A61K 31/16* (2013.01); *A61K 31/165* (2013.01); *A61K 31/166* (2013.01); *A61K 31/167* (2013.01); *A61K 31/433* (2013.01); *A61K 31/4965* (2013.01); *A61K 31/65* (2013.01); *C07C 233/18* (2013.01); *C07C 233/25* (2013.01); *C07C 233/29* (2013.01); *C07C 233/73* (2013.01); *C07C 235/40* (2013.01); *C07C 235/60* (2013.01); *C07C 235/66* (2013.01); *C07C 235/82* (2013.01); *C07C 235/84* (2013.01); *C07D 285/135* (2013.01); *C07D 295/192* (2013.01); *C07C 2101/14* (2013.01); *C07C 2102/10* (2013.01); *C07C 2103/24* (2013.01)

(58) Field of Classification Search
CPC .......................... A61K 31/495; C07C 233/18
See application file for complete search history.

(56) References Cited

U.S. PATENT DOCUMENTS 3,725,543 A * 4/1973 Konopka ............. A23K 20/195
424/114
5,298,502 A    3/1994 Halling et al.

FOREIGN PATENT DOCUMENTS

| CH | 631 158 A5 | 7/1982 |
| DE | 29 01 630 | 7/1980 |
| EP | 2 008 530 | 12/2008 |

(Continued)

OTHER PUBLICATIONS

Barbosa Filho, J., et al., "Synthesis of Several New Phenylethylamides of Substituted Benzoic Acids," *Quimica Nova* 13(4):332-334 (1990).

(Continued)

*Primary Examiner* — Wu-Cheng Winston Shen
*Assistant Examiner* — Christopher R Stone
(74) *Attorney, Agent, or Firm* — Medler Ferro Woodhouse & Mills PLLC

(57) ABSTRACT

The invention relates to compounds and pharmaceutical compositions useful in combination with tetracyclines in the treatment of bacterial infections caused by Gram-positive and Gram-negative pathogens, with particular efficacy in tetracycline resistant strains. These compounds specifically bind to TetR and therefore prevent the transcriptional activation of tet resistance genes. The compounds have a potentiating effect on the activity of members of the tetracycline family, in particular of tetracycline, minocycline, doxycycline and tigecycline, in the treatment of tetracycline susceptible, intermediate and tetracycline resistant pathogens.

10 Claims, No Drawings

(56) References Cited

FOREIGN PATENT DOCUMENTS

| FR | 2 783 519 | 3/2000 |
|----|-----------|--------|
| JP | 2 115838  | 4/1990 |

OTHER PUBLICATIONS

Chen, I., et al., "Amides with Anti-Platelet Aggregation Activity from Piper taiwanense," *Fitoterapia* 78:414-419 (2007).
Chouhan, H., et al., "2D-Quantitative Structure Property Relationship Study of N-(Aryl)-2-thiopene-2-ylacetamide Derivatives as Antitubercular Agents," *Asian Journal of Chem.* 22:4675-4680 (2010).
Einhorn et al., "Ueber N-Methylolverbindungen der Säureamide," *Justus Liebigs Annalen der Chemie 343*:223-263 (1905).
Frénois, F., et al., "Structure of EthR in a Ligand Bound Conformation Reveals Therapeutic Perspectives against Tuberculosis," *Molecular Cell* 16:301-307 (2004).
Fritzson, I., et al., N-Substituted Salicylamides as Selective Malaria Parasite Dihydroorotate Dehydrogenase Inhibitors, *Med. Chem. Commun.* 2:895-898 (2011).
Govindachari, T.R., et al., "The Isoquinoline Series. II. Synthesis of some 5, 6- and 5, 8-dimethoxyisoquinolines," *Chem. Abstracts, Database accession No. 1958*:61211 (1958).
Henssler, E., et al., "Tet Repressor Mutants with Altered Effector Binding and Allostery," *FEBS Journal 272*:4487-4496 (2005).
McCaskill, E. S., et al., "Electrochemical Properties and Mechanisms of Action of Developers in Spectra Film," *Chem. Abstracts, Database accession No. 1989*:621899 (1989).
Orjala, J., et al., "Aduncamide, A Cytotoxic and Antibacterial β-Phenylethylamine-Derived Amide from Piper Aduncum," *Natural Product Letters*, 2:231-236 (1993).
Patent Abstracts of Japan, English language Abstract of Japanese Patent Publication No. 02115838, published Apr. 27, 1990.
Satoh, T., et al., "Comparison of the Inhibitory Action of Synthetic Capsaicin Analogues with Various NADH-ubiquinone Oxidoreductases," *Biochimica et Biophysica Acta 1273*:21-30 (1996).
Schubert, H., et al., "Synthese and Oxydation von unsymmetrisch verbrückten Dihydrochinonen," *Journal Fuer Praktische Chemie 319*:745-754 (1977).
Zakeri, B., et al., "Chemical Biology of Tetracycline Antibiotics," *Biochem. Cell Biol.* 86:124-136 (2008).
PCT/EP2014/05/2012 International Search Report, (May 14, 2014).

\* cited by examiner

COMPOSITION FOR TREATMENT OF PATHOGENS THAT ARE RESISTANT TO TETRACYCLINES

FIELD OF THE INVENTION

The invention relates to compounds and pharmaceutical compositions useful in combination with tetracyclines in the treatment of bacterial infections caused by Gram-positive and Gram-negative pathogens, with particular efficacy in tetracycline resistant strains. The invention further relates to a method of treating bacterial infections.

BACKGROUND OF THE INVENTION

The global problem of antimicrobial resistance is well recognized by national authorities and rated as a major threat of the 21$^{st}$ century (for a review see Boucher H. et al., Clinical Infectious Diseases 2009, 48(1), 1-12). In contrast to de novo antibiotic development, efforts on alternative approaches such as antibiotic potentiators—following the Augmentin paradigm—have been intensified. The pathogens that cause major problems especially in hospital environments are often summarized as ESKAPE group of opportunistic bacteria (*Enterococcus faecium, Staphylococcus aureus, Klebsiella pneumoniae, Acinetobacter baumanni, Pseudomonas aeruginosa*, and *Enterobacter* species (Rice L., *The Journal of Infectious Diseases* 2008, 197(8), 1079-1081), which needs to be expanded with *Clostridium difficile*. Multi-resistant or extensively drug resistant isolates belonging to this group are increasingly hard to treat, and there exists a raising number of untreatable strains. The only limiting factor in treatment of these pathogens with the existing portfolio of antibiotics is the antimicrobial resistance. Antibiotics that have been prescribed by physicians for decades due to their preferable efficacy or toxicity profile thus had to be largely replaced.

Tetracyclines are proven antibacterial agents and represent one of the most trusted classes of antibiotics. Discovered in the 1940s, the tetracyclines are a family of antibiotics that inhibit protein synthesis by preventing the attachment of aminoacyl-tRNA to the ribosomal acceptor (A) site (Griffin M. O. et al., *American Journal of Physiology. Cell Physiology* 2010, 299(3), C539-48).

The tetracycline class of antibiotics comprises a distinct family of substituted tetracyclic hydronaphthalene compounds produced by strains of *Streptomyces aureofaciens* and *Streptomyces rimosus*. First generation tetracyclines such as tetracycline, chlortetracycline, oxytetracycline, and demeclocycline are obtained by biosynthesis. Second generation tetracyclines such as doxycycline, lymecycline, meclocycline, methacycline, minocycline, and rolitetracycline are derivatives obtained by semi-synthesis. Third generation tetracyclines such as tigecycline (Tygacil® Pfizer), pentacycline antibacterials (a structural modification of doxycycline with five rings), azatetracyclines and fluorocyclines (heteroatoms inserted into the D ring), and alkylaminotetracycline antibacterials, are obtained by total synthesis. Although some researchers consider tigecycline to be distinct from other tetracyclines drugs and representing a new family of antibacterials called glycylcyclines, these glycylcyclines are considered tetracyclines for the purpose of the present invention.

Tetracyclines display broad spectrum bacteriostatic activity in Gram-negative and Gram-positive pathogens. Today, there are 61 tetracycline resistance genes sequenced, which are often located on mobile elements and encode for three major mechanisms of resistance: i) tetracycline efflux, ii) ribosomal protection, and iii) tetracycline modification (Thaker M. et al., *CMLS* 2010, 67(3), 419-31).

i) Tetracycline efflux proteins belong to the major facilitator superfamily and are found in both Gram-positive and Gram-negative bacteria. According to their sequence homology, the efflux proteins are divided into 5 groups: Group 1: Tet(A), Tet(B), Tet(C), Tet(D), Tet(E), Tet(G), Tet(H), Tet(J), Tet(Z), and Tet(30); Group 2: Tet(K) and Tet(L); Group 3: Otr(B) and Tcr(3); Group 4: TetA(P); Group 5: Tet(V); and the non-classified Tet(31), Tet(33), Tet(V), Tet(Y), Tet(34), and Tet(35).

ii) Ribosomal protection proteins share homology with the elongation factors EF-Tu and EF-G and cause a change in conformation of the ribosome after binding, thus preventing tetracycline binding. Members of ribosomal protection proteins are: Tet(M), Tet(0), Tet(S), Tet(W), Tet(32), Tet(36), Tet(Q), Tet(T), Otr(A), and TetB(P).

iii) Tetracycline modification proteins include the enzymes Tet(37) and Tet(X), both of which inactivate tetracycline.

The expression of several of these tet genes is controlled by a family of tetracycline transcriptional regulators known as TetR. TetR family regulators are involved in the transcriptional control of multidrug efflux pumps, pathways for the biosynthesis of antibiotics, response to osmotic stress and toxic chemicals, control of catabolic pathways, differentiation processes, and pathogenicity (Ramos J. L. et al., *Microbiology and Molecular Biology Reviews* 2005, 69(2), 326-356). The TetR proteins identified in over 115 genera of bacteria and archaea share a common helix-turn-helix (HTH) structure in their DNA-binding domain. However, TetR proteins can work in different ways: they can bind a target operator directly to exert their effect (e.g. TetR binds Tet(A) gene to repress it in the absence of tetracycline), or they can be involved in complex regulatory cascades in which the TetR protein can either be modulated by another regulator, or TetR can trigger the cellular response. Most of the defense mechanisms have only transient benefit that is coupled to an associated biological cost. Thus, resistance gene expression is often tightly regulated at the transcriptional or translational level and often triggered by the antibiotic itself.

In the absence of the antibiotic (or antibiotic induced stress signals), the repressor protein is bound to its cognate operator sequence and therefore repressing the transcription of resistance genes. Addition of the antibiotic removes the transcriptional block with subsequent expression of resistance genes.

A Transcriptional Regulator Inhibitory Compound (TRIC) is predicated on the identification of small inhibitory compounds that efficiently block the function of bacterial resistance genes at the highest-possible level, i.e. their transcription. At this point, in general two different interventions exist: (i) inhibitory binding of an activator to its cognate sequence and (ii) constant binding of a repressor to the DNA. Most of the bacterial resistance pathways follow the repressor model (ii), where activation of resistance genes only occurs when the repressor is removed from the DNA.

SUMMARY OF THE INVENTION

The invention relates to TetR binding compounds and pharmaceutical compositions comprising these, useful in combination with tetracyclines in the treatment of bacterial infections caused by Gram-positive and Gram-negative pathogens, with particular efficacy in tetracycline resistant strains. These compounds specifically bind to TetR and therefore prevent the transcriptional activation of tet resistance genes. The compounds have a potentiating effect on the activity of members of the tetracycline family, in particular of tetracycline, minocycline, doxycycline and tigecycline, in the treatment of tetracycline susceptible, intermediate and tetracycline resistant pathogens.

In particular the invention relates to pharmaceutical compositions comprising compounds of formula (1), (2), (3) or (4), which are derivatives of a hydroquinone incorporating a benzamide or related carboxamide function, and one or more tetracyclines. Furthermore the invention relates to novel compounds of formula (1), (2), (3) and (4) as such, and to pharmaceutical compositions comprising compounds of formula (1), (2), (3) or (4).

Furthermore the invention relates to a method of treating bacterial infections comprising administering to a patient in need thereof a therapeutically effective amount of a mixture of a compound of formula (1), (2), (3) or (4) with one or more tetracyclines.

DETAILED DESCRIPTION OF THE INVENTION

The invention relates to TetR binding compounds and pharmaceutical compositions comprising these. In particular, the invention relates to pharmaceutical compositions comprising a compound of formula (1), (2), (3) or (4), to such pharmaceutical compositions further comprising one or more tetracyclines. and to novel compounds of formula (1), (2), (3) and (4) as defined hereinafter. The invention is based on the observation that a compound preventing TetR from dissociation of the tetO operator sequence in the presence of the inducing antibiotic tetracycline or another member of the tetracycline family of antibiotics, for example minocycline or doxycycline, substantially increases the activity of the corresponding tetracyclines in clinical isolates of *Staphylococcus aureus*, *Enterococcus faecalis*, *Escherichia coli*, *Acinetobacter baumanii* and *Klebsiella pneumoniae*.

In particular the invention relates to pharmaceutical compositions comprising TetR binding compounds of formula

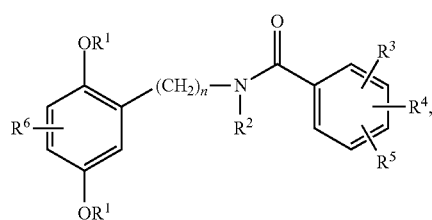
(1)

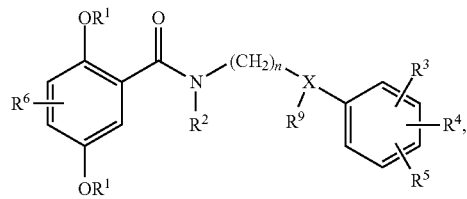
(2)

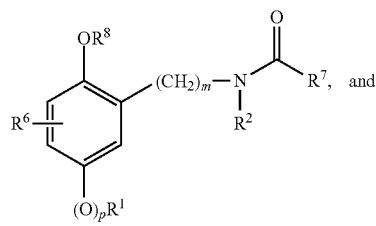
(3)

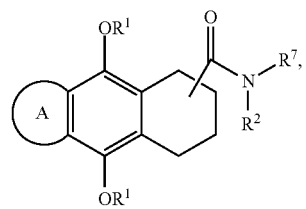
(4)

wherein
$R^1$ is hydrogen or methyl;
$R^2$ is hydrogen or methyl;
$R^3$, $R^4$ and $R^5$ are, independently of each other, hydrogen, lower alkyl, halo-lower alkyl, halogen, cyano, hydroxy, lower alkoxy, halo-lower alkoxy, phenoxy, amino, lower alkylamino, di-(lower alkyl)amino, optionally substituted lower alkylcarbonylamino, carboxy, lower alkylcarbonyl, lower alkoxycarbonyl, phenylcarbonyl, or phenyl;
$R^6$ is hydrogen, phenoxy or phenyl;
$R^7$ is alkyl, cyclohexyl-lower alkyl, optionally substituted phenyl or phenyl-lower alkyl, or optionally substituted heteroaryl or heteroaryl-lower alkyl;
$R^8$ is hydrogen, methyl, phenyl or halophenyl;
A is a benzo ring, 1,4-dioxobenzo ring, phenylcarbonyl in either of the two positions of the A ring connection, or absent;
X is CH or N;
$R^9$ is hydrogen or methyl, if X is CH; or $R^2$ and $R^9$ together represent ethylene, if X is N;
n is 1, 2, 3 or 4;
m is 0 or 1; and
p is 0 or 1.
More particularly, the invention relates to compounds of formula (2), (3) and (4) as defined hereinbefore.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

The invention relates also to possible tautomers of compounds of formula (1), (2), (3) or (4).

Alkyl has from 1 to 12, preferably from 1 to 7 carbon atoms, and is linear or branched. Alkyl is preferably lower alkyl.

Lower alkyl has 1 to 7, preferably 1 to 4 carbon atoms and is butyl, such as n-butyl, sec-butyl, isobutyl, tert-butyl, propyl, such as n-propyl or isopropyl, ethyl or methyl. Preferably lower alkyl is $C_1$-$C_4$-alkyl, in particular methyl or ethyl.

In optionally substituted phenyl, substituents are preferably lower alkyl, halo-lower alkyl, lower alkoxy-lower alkyl, hydroxy, lower alkoxy, halo-lower alkoxy, lower alkoxy-lower alkoxy, methylenedioxy, hydroxysulfonyloxy, phenoxy, halophenoxy, carboxy, lower alkoxycarbonyl, aminocarbonyl, hydroxysulfonyl, aminosulfonyl, phenyl, halophenyl, hydroxyphenyl, halo, cyano or nitro, in particular lower alkyl, halo-lower alkyl, hydroxy, lower alkoxy, phenoxy, halophenoxy, phenyl or halo.

Halophenyl is preferably fluoro- or chlorophenyl, in particular p-chlorophenyl.

Heteroaryl represents an aromatic group containing at least one heteroatom selected from nitrogen, oxygen and sulfur, and is mono- or bicyclic, optionally carrying substituents. Monocyclic heteroaryl includes 5 or 6 membered heteroaryl groups containing 1, 2, 3 or 4 heteroatoms selected from nitrogen, sulfur and oxygen. Bicyclic heteroaryl includes 9 or 10 membered fused-ring heteroaryl groups. Examples of heteroaryl include pyrrolyl, thienyl, furyl, pyrazolyl, imidazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, and benzo or pyridazo fused derivatives of such monocyclic heteroaryl groups, such as indolyl, benzimidazolyl, benzofuryl, quinolinyl, isoquinolinyl, quinazolinyl, pyrrolopyridine, imidazopyridine, or purinyl, all optionally substituted. Preferably, heteroaryl is pyridyl, pyrimdinyl, pyrazinyl, pyridazinyl, thienyl, pyrazolyl, imidazolyl, thiazolyl, oxadiazolyl, triazolyl, oxazolyl, isoxazolyl, isothiazolyl, thiadiazolyl, pyrrolyl, indolyl, pyrrolopyridine or imidazopyridine; in particular thiadiazolyl. Substituents considered are those mentioned above as substituents for phenyl, in particular lower alkyl, halo-lower alkyl, lower alkoxy-lower alkyl, hydroxy, lower alkoxy, halo-lower alkoxy, lower alkoxy-lower alkoxy, phenoxy, hydroxyphenoxy, halophenoxy, phenyl, halophenyl, hydroxyphenyl, halo, cyano or nitro, in particular lower alkyl, halo-lower alkyl, lower alkoxy, phenoxy, halophenoxy, phenyl, halophenyl, hydroxyphenyl, or halo.

Halo-lower alkyl is preferably fluoro-lower alkyl, especially trifluoromethyl, 2,2,2-trifluoroethyl or pentafluoroethyl.

Halogen is fluorine, chlorine, bromine, or iodine, in particular fluorine and chlorine.

Lower alkoxy is especially methoxy, ethoxy, isopropyloxy, or tert-butyloxy. Halo-lower alkoxy is preferably fluoro-lower alkoxy, especially difluoromethoxy.

Phenyl-lower alkyl includes phenyl and lower alkyl as defined hereinbefore, and is e.g. benzyl, 1-phenethyl, 2-phenethyl, or 3-phenylpropyl.

Heteroaryl-lower alkyl includes heteroaryl and lower alkyl as defined hereinbefore, and is e.g. 2-, 3- or 4-pyridylmethyl, 1- or 2-pyrrolylmethyl, 1-pyrazolylmethyl, 1-imidazolylmethyl, 2-(1-imidazolyl)ethyl or 3-(1-imidazolyl) propyl.

Optionally substituted lower alkylcarbonylamino is especially methyl- or ethyl-carbonylamino, methoxymethylcarbonylamino, halomethylcarbonylamino, cyanomethylcarbonylamino, or tert-butylaminomethylcarbonylamino.

Salts are especially the pharmaceutically acceptable salts.

Particular salts considered are those replacing hydrogen in a carboxylic acid function. Suitable cations are, e.g., sodium, potassium, calcium, magnesium or ammonium cations, or also cations derived by protonation from primary, secondary or tertiary amines containing, for example, lower alkyl, hydroxy-lower alkyl or hydroxy-lower alkoxy-lower alkyl groups, e.g., 2-hydroxyethylammonium, 2-(2-hydroxyethoxy)ethyldimethyl-ammonium, diethylammonium, di(2-hydroxyethyl)ammonium, trimethylammonium, triethylammonium, 2-hydroxyethyldimethylammonium, or di(2-hydroxyethyl)methyl-ammonium, also from correspondingly substituted cyclic secondary and tertiary amines, e.g., N-methylpyrrolidinium, N-methylpiperidinium, N-methylmorpholinium, N-2-hydroxy-ethylpyrrolidinium, N-2-hydroxyethylpiperidinium, or N-2-hydroxyethylmorpholinium, and the like.

If the compounds contain a basic nitrogen atom, salts are especially pharmaceutically acceptable acid addition salts of such basic compounds. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethanesulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compounds of formula (1), (2), (3) and (4) have valuable pharmacological properties. The invention also relates to these compounds and salts as defined hereinbefore for use as medicaments in combination with tetracyclines. A compound according to the invention shows prophylactic and therapeutic efficacy in combination with tetracyclines especially against bacterial infections caused by Gram-positive and Gram-negative pathogens with particular efficacy in tetracycline resistant bacterial strains. These compounds specifically bind to TetR and therefore prevent the transcriptional activation of tet resistance genes.

The compounds have a potentiating effect on the activity of tetracycline and other antibiotics of the tetracycline family, such as minocycline, doxycycline and tigecycline, in the treatment of tetracycline susceptible, intermediate and tetracycline resistant pathogens.

Particularly preferred is the use of a compound of formula (1), (2), (3) or (4) or a salt thereof according to the invention as a medicament in combination with tetracyclines for the prevention and treatment of tetracycline susceptible, intermediate and, in particular, tetracycline resistant bacterial infections caused by Gram-positive and Gram-negative bacterial pathogens. Such pathogens are Gram-positive pathogens such as *Actinobacteria, Actinomyces, Actinomyces israelii, Bacillales, Bacillus, Clostridium, Clostridium acetobutylicum, Clostridium aerotolerans, Clostridium*

*argentinense, Clostridium baratii, Clostridium beijerinckii, Clostridium bifermentans, Clostridium botulinum, Clostridium butyricum, Clostridium cadaveris, Clostridium cellulolyticum, Clostridium chauvoei, Clostridium clostridioforme, Clostridium colicanis, Clostridium difficile, Clostridium estertheticum, Clostridium fallax, Clostridium formicaceticum, Clostridium histolyticum, Clostridium innocuum, Clostridium kluyveri, Clostridium ljungdahlii, Clostridium novyi, Clostridium paraputrificum, Clostridium perfringens, Clostridium phytofermentans, Clostridium piliforme, Clostridium ragsdalei, Clostridium ramosum, Clostridium scatologenes, Clostridium septicum, Clostridium sordellii, Clostridium sporogenes, Clostridium sticklandii, Clostridium tertium, Clostridium tetani, Clostridium thermosaccharolyticum, Clostridium tyrobutyricum, Corynebacterium, Corynebacterium bovis, Corynebacterium diphtheriae, Corynebacterium granulosum, Corynebacterium jeikeium, Corynebacterium minutissimum, Corynebacterium renale, Enterococcus faecalis, Enterococcus faecium, Lactobacillales, Listeria, Nocardia asteroides, Nocardia brasiliensis, Nocardia farcinica, Propionibacterium acnes, Rhodococcus equi, Sarcina* (genus), *Solobacterium moorei, Staphylococcus aureus, Staphylococcus capitis, Staphylococcus caprae, Staphylococcus epidermidis, Staphylococcus haemolyticus, Staphylococcus hominis, Staphylococcus lugdunensis, Staphylococcus muscae, Staphylococcus nepalensis, Staphylococcus pettenkoferi, Staphylococcus saprophyticus, Staphylococcus succinus, Staphylococcus warneri, Staphylococcus xylosus, Streptococcus agalactiae, Streptococcus anginosus, Streptococcus bovis, Streptococcus canis, Streptococcus iniae, Streptococcus lactarius, Streptococcus mitis, Streptococcus mutans, Streptococcus oralis, Streptococcus parasanguinis, Streptococcus peroris, Streptococcus pneumoniae, Streptococcus pyogenes, Streptococcus ratti, Streptococcus salivarius, Streptococcus sanguinis, Streptococcus sobrinus, Streptococcus suis, Streptococcus salivarius* subsp. *thermophilus, Streptococcus uberis, Streptococcus vestibularis*, and *Streptococcus viridians*, and Gram-negative pathogens such as *Acetobacter aceti, Acetobacter xylinum, Acinetobacter baumanii, Magnetospirillum magnetotacticum, Helicobacter pylori, Chromatium okenii, Thiocapsa literalis, Thiocapsa purpurea, Rhodobacter sphaeroides, Rhodospirillum rubrum, Rhodocyclus tenuis, Methylococcus capsulatus, Methylobacter albus, Methylomonas methanica, Aliivibrio fischeri, Photobacterium phosphoreum, Vibrio harveyi, Photococcus caeruleum, Nitrosomonas europaea, Nitrobacter vulgaris, Nitrobacter hamburgensis, Nitrococcus mobilis, E. coli, Salmonella typhimurium, Shigella dysenteriae, Yersinia pestis, Klebsiella pneumoniae, Serratia marcescens, Vibrio cholerae, Neisseria gonorrhoeae, Acinetobacter baumannii, Moraxella bovis, Pseudomonas aeruginosa, Azotobacter vinelandii*, and *Rickettsia rickettsia*.

Of particular interest is the treatment of infections caused by tetracycline susceptible and in particular tetracycline resistant pathogens of the ESKAPE group of clinically relevant pathogens, such as *Staphylococcus aureus, Staphylococcus epidermidis, Staphylococcus haemolyticus, Streptococcus pneumonia, Streptococcus pyogenes, Streptococcus sanguinis, Enterococcus faecalis, Enterococcus faecium, Clostridium difficile, Acinetobacter baumanii, Escherichia coli, Enterobacter cloacae, Klebsiella pneumonia* and *Pseudomonas aeruginosa*. Regarding the current medical use of tetracyclines in human and veterinary therapies the combination of compounds of formula (1), (2), (3) or (4) with tetracyclines in the treatment of infections of the urinary tract, the intestines and with *chlamydia*, especially in patients allergic to β-lactams and macrolides is of high relevance due to widespread development of resistance in the causative organisms. Additionally the use in the treatment of moderately severe acne and rosacea is considered, together with tetracycline, oxytetracycline, doxycycline, or minocycline.

Doxycycline in combination with compounds of formula (1), (2), (3) or (4) is also used as a prophylactic treatment for infection by *Bacillus anthracis* (anthrax) and is effective against *Yersinia pestis*, the infectious agent of bubonic plague. It can also be used for malaria treatment and prophylaxis, as well as for treating elephantiasis. Tetracyclines in combination with compounds of formula (1), (2), (3) or (4) are the treatment of choice for infections caused by *chlamydia* (trachoma, psittacosis, salpingitis, urethritis, and L. venereum infection), *Rickettsia* (typhus, Rocky Mountain spotted fever), brucellosis, and spirochetal infections (borreliosis, syphilis, and Lyme disease). In addition, they may be used to treat anthrax, plague, tularemia, and Legionnaires' disease.

A compound of formula (1), (2), (3) or (4) is administered in combination with one or more tetracyclines, the combination therapy taking the form of fixed combinations, or the administration of a compound of the invention and one or more tetracyclines being staggered or given independently of one another.

Therapeutic agents selected from tetracyclines for possible combination are especially tetracycline, oxytetracycline, chlorotetracycline, demeclocycline, meclocycline, rolitetracycline, 6-thiatetracycline, 4-epi-anhydrochlortetracycline, aminomethylcycline, azatetracycline, fluorocycline, pentacycline, minocycline, doxycycline and glycylcyclines, in particular tigecycline.

With the groups of preferred compounds of formula (1), (2), (3) or (4) mentioned hereinafter, definitions of substituents from the general definitions mentioned hereinbefore may reasonably be used, for example, to replace more general definitions with more specific definitions or especially with definitions characterized as being preferred.

In particular, the invention refers to compounds per se and to a pharmaceutical compositions comprising such compounds of formula (1), (2), (3) and (4), wherein $R^1$ is hydrogen or methyl;

$R^2$ is hydrogen or methyl;

$R^3$ and $R^4$ are, independently of each other, hydrogen, lower alkyl, preferably n-butyl, sec-butyl, tert-butyl, propyl, isopropyl, ethyl, or methyl; halo-lower alkyl, preferably fluoro-lower alkyl, especially trifluoromethyl, 2,2,2-trifluoroethyl, or pentafluoroethyl; halogen, preferably fluorine, chlorine or bromine; cyano, lower alkoxy, preferably methoxy, ethoxy, isopropyloxy, or tert-butyloxy; halo-lower alkoxy, preferably difluoromethoxy; optionally substituted lower alkylcarbonylamino, preferably methoxymethylcarbonylamino, cyanomethylcarbonylamino, tert-butylaminomethylcarbonylamino; or phenyl;

$R^5$ is hydrogen, methyl, trifluoromethyl, fluorine, chlorine or cyano;

$R^6$ is hydrogen, phenoxy or phenyl;

$R^7$ is lower alkyl, cyclohexyl-lower alkyl, preferably cyclohexylmethyl or cyclohexylethyl; phenyl, unsubstituted or substituted by one, two or three substituents selected from lower alkyl, preferably n-butyl, sec-butyl, tert-butyl, propyl, isopropyl, ethyl, or methyl; halo-lower alkyl, preferably fluoro-lower alkyl, especially trifluoromethyl, 2,2,2-trifluoroethyl, or pentafluoroethyl; halogen, preferably fluorine, chlorine or bromine; cyano, hydroxy, lower alkoxy, preferably methoxy, ethoxy, isopropyloxy, or tert-butyloxy; halo-lower alkoxy, preferably difluoromethoxy; phenoxy, halophenoxy, or phenyl; phenyl-lower alkyl, preferably phenylmethyl, 2-phenylethyl or 3-phenylpropyl, wherein phenyl is unsubstituted or substituted by one, two or three substituents selected from lower alkyl, preferably n-butyl, sec-butyl, tert-butyl, propyl, isopropyl, ethyl, or methyl; halo-lower alkyl, preferably fluoro-lower alkyl, especially trifluoromethyl, 2,2,2-trifluoroethyl, or pentafluoroethyl; halogen, preferably fluorine, chlorine or bromine; cyano, hydroxy, lower alkoxy, preferably methoxy, ethoxy, isopropyloxy, or tert-butyloxy; halo-lower alkoxy, preferably difluoromethoxy; phenoxy, halophenoxy, or phenyl; or thiadiazolyl substituted by phenyl, trifluoromethylphenyl, halophenyl or hydroxyphenyl;

$R^8$ is hydrogen, methyl, phenyl or halophenyl;

A is a benzo ring, 1,4-dioxobenzo ring, phenylcarbonyl in either of the two positions of the A ring connection, or absent;

X is CH or N;

$R^9$ is hydrogen or methyl, if X is CH; or $R^2$ and $R^9$ together represent ethylene, if X is N;

n is 1, 2, 3 or 4;

m is 0 or 1; and p is 0 or 1.

The invention preferably relates to such pharmaceutical compositions comprising a compound of formula (1) wherein n is 3 or 4, and to such compounds of formula (1) wherein n is 3 or 4 per se.

Furthermore, the invention refers preferably to pharmaceutical compositions comprising compounds of formula (1), wherein $R^1$ is hydrogen;

$R^2$ is hydrogen or methyl;

$R^3$ and $R^4$ are, independently of each other, hydrogen, methyl, ethyl, propyl, isopropyl, isobutyl, tert-butyl, trifluoromethyl, 2,2,2-trifluoroethyl, fluorine, chlorine, bromine, cyano, methoxy, ethoxy, methoxymethylcarbonylamino, cyanomethylcarbonylamino, or tert-butylaminomethylcarbonylamino;

$R^5$ is hydrogen;

$R^6$ is hydrogen, phenoxy or phenyl; and n is 1, 2, 3 or 4;

in particular to such compositions wherein $R^3$ is hydrogen, methyl, ethyl, propyl, isopropyl, isobutyl, tert-butyl, trifluoromethyl, 2,2,2-trifluoroethyl, fluorine, chlorine, bromine, cyano, methoxy, ethoxy, methoxymethylcarbonylamino, cyanomethylcarbonylamino, or tert-butylaminomethylcarbonylamino;

$R^4$ is fluoro or trifluoromethyl;

and to such compounds of formula (1) per se wherein $R^3$ is hydrogen, methyl, ethyl, propyl, isopropyl, isobutyl, tert-butyl, trifluoromethyl, 2,2,2-trifluoroethyl, fluorine, chlorine, bromine, cyano, hydroxy, methoxy, ethoxy, methoxymethylcarbonylamino, cyanomethylcarbonylamino, or tert-butylaminomethylcarbonylamino; and $R^4$ is fluoro or trifluoromethyl.

More preferably, the invention refers to compounds per se and to a pharmaceutical composition comprising such compounds of formula (2), wherein $R^1$ is hydrogen;

$R^2$ is hydrogen or methyl;

$R^3$ and $R^4$ are, independently of each other, hydrogen, methyl, ethyl, propyl, isopropyl, isobutyl, tert-butyl, trifluoromethyl, 2,2,2-trifluoroethyl, fluorine, chlorine, bromine, cyano, methoxy, ethoxy, methoxymethylcarbonylamino, cyanomethylcarbonylamino, or tert-butylaminomethylcarbonylamino;

$R^5$ is hydrogen; and $R^6$ is hydrogen, phenoxy or phenyl;

X is CH or N;

$R^9$ is hydrogen or methyl, if X is CH; or $R^2$ and $R^9$ together represent ethylene, if X is N; and n is 2, 3 or 4, if X is CH; or n is 2, if X is N;

in particular to such compositions and compounds per se wherein X is N and n is 2.

Likewise, the invention refers preferably to compounds per se and to a pharmaceutical composition comprising such compounds of formula (3), wherein $R^1$ is hydrogen;

$R^2$ is hydrogen or methyl;

$R^6$ is hydrogen, phenoxy or phenyl;

$R^7$ is lower alkyl or phenyl-lower alkyl, wherein phenyl is unsubstituted or substituted by lower alkyl, halo-lower alkyl, hydroxy, lower alkoxy, phenoxy, halophenoxy, or phenyl;

$R^8$ is hydrogen, methyl, phenyl or halophenyl;

m is 0 or 1; and p is 0 or 1;

in particular to such compositions and compounds wherein p is 0.

Likewise, the invention refers preferably to compounds per se and to a pharmaceutical composition comprising such compounds of formula (4), wherein $R^1$ is hydrogen;

$R^2$ is hydrogen or methyl;

$R^7$ is lower alkyl, preferably n-butyl, sec-butyl, tert-butyl, n-propyl, isopropyl, ethyl or methyl, cyclohexyl-lower alkyl, preferably cyclohexylmethyl or cyclohexylethyl; phenyl, unsubstituted or substituted by one or two substituents selected from lower alkyl, preferably ethyl or methyl; halo-lower alkyl, preferably fluoro-lower alkyl, especially trifluoromethyl, 2,2,2-trifluoroethyl, or pentafluoroethyl; halogen, preferably fluorine or chlorine; hydroxy, lower alkoxy, preferably methoxy or ethoxy; phenoxy, halophenoxy, preferably fluorophenoxy or chlorophenoxy; or phenyl; phenyl-lower alkyl, preferably phenylmethyl, 2-phenylethyl or 3-phenylpropyl, wherein phenyl is unsubstituted or substituted by one or two substituents selected from lower alkyl, preferably ethyl or methyl; halo-lower alkyl, preferably fluoro-lower alkyl, especially trifluoromethyl, 2,2,2-trifluoroethyl, or pentafluoroethyl; halogen, preferably fluorine or chlorine; hydroxy, lower alkoxy, preferably methoxy or ethoxy; phenoxy, halophenoxy, preferably fluorophenoxy or chlorophenoxy, or phenyl; or thiadiazolyl substituted by phenyl, trifluoromethylphenyl, halophenyl or hydroxyphenyl; and A is a benzo ring, 1,4-dioxobenzo ring, phenylcarbonyl in either of the two positions of the A ring connection, or absent.

Most preferred are the compounds of the examples.

A compound of the invention may be prepared by processes that, though not applied hitherto for the new compounds of the present invention, are known per se, in particular processes as described in the Examples. If so desired, an obtainable compound of formula (1), (2), (3) or (4) is converted into another compound of formula (1), (2), (3) or (4), a free compound of formula (1), (2), (3) or (4) is converted into a salt, an obtainable salt of a compound of formula (1), (2), (3) or (4) is converted into the free compound or another salt, and/or a mixture of isomeric compounds of formula (1), (2), (3) or (4) is separated into the individual isomers.

In the mentioned processes, protecting groups may be used. The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end products. The specialist knows, or can easily establish, which protecting groups are suitable with the reactions mentioned.

The protection of such functional groups by such protecting groups, the protecting groups themselves, and their removal reactions are described for example in standard reference books for peptide synthesis and in special books on protective groups such as T. W. Greene & P. G. M. Wuts, "Protective Groups in Organic Synthesis", Wiley, 3$^{rd}$ edition 1999.

In the additional process steps, carried out as desired, functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

In the conversion of an obtainable compound of formula (1), (2), (3) or (4) into another compound of formula (1), (2), (3) or (4), an amino group may be alkylated or acylated to give the correspondingly substituted compounds. Alkylation may be performed with an alkyl halide or an activated alkyl ester. For methylation, diazomethane may be used. Alkylation may also be performed with an aldehyde under reducing conditions. For acylation the corresponding acyl chloride is preferred. Alternatively, an acid anhydride may be used, or acylation may be accomplished with the free acid under conditions used for amide formation known per se in peptide chemistry, e.g. with activating agents for the carboxy group, such as 1-hydroxybenzotriazole, optionally in the presence of suitable catalysts or co-reagents. Furthermore amine may be transformed into heteroaryl and heterocyclyl under reaction conditions typical for such cyclizations.

A hydroxy group may be alkylated (etherified) or acylated (esterified) to give the correspondingly substituted compounds in a procedure related to the one described for an amino group. Alkylation may be performed with an alkyl halide or an activated alkyl ester. For methylation, diazomethane may be used. For acylation the corresponding acyl chloride or acid anhydride may be used, or acylation may be accomplished with the free acid and a suitable activating agent.

Reduction of a nitro group in a nitro-substituted aryl or heteroaryl group to give the corresponding amino group is done, e.g., with iron powder in alcohol or with other reducing agents.

A carboxy group in a carboxy-substituted aryl or heteroaryl group may be amidated under conditions used for amide formation known per se in peptide chemistry, e.g. with the corresponding amine and an activating agent for the carboxy group, such as 1-hydroxybenzotriazole, optionally in the presence of suitable catalysts or co-reagents.

A chloro, bromo or iodo substitutent in an aryl or heteroaryl group may be replaced by phenyl or a phenyl derivative by reaction with a suitable phenylboronic acid in a Suzuki reaction as described above.

Salts of a compound of formula (1), (2), (3) or (4) may be prepared in a manner known per se., e.g. by treatment with an inorganic or organic base, for example with alkali metal carbonates, alkali metal hydrogencarbonates, or alkali metal hydroxides, typically potassium carbonate or sodium hydroxide.

Salts can usually be converted to free compounds, e.g. by treating with suitable acids.

It should be emphasized that reactions analogous to the conversions mentioned in this chapter may also take place at the level of appropriate intermediates.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralising agents, for example ion exchangers, typically cation exchangers, for example in the H$^+$ form, depending on the type of reaction and/or reactants at reduced, normal, or elevated temperature, for example in the range from −100° C. to about 190° C., preferably from about −80° C. to about 150° C., for example at −80 to +60° C., at −20 to +40° C., at room temperature, or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric mixtures.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and further processes the said compound in situ. In the preferred embodiment, one starts from those starting materials which lead to the compounds described hereinabove as preferred, particularly as especially preferred, primarily preferred, and/or preferred above all.

In the preferred embodiment, a compound of formula (1), (2), (3) or (4) is prepared according to or in analogy to the processes and process steps defined in the Examples.

The compounds of formula (1), (2), (3) or (4), including their salts, are also obtainable in the form of hydrates, or their crystals can include for example the solvent used for crystallization, i.e. be present as solvates.

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials are known, commercially available, or can be synthesized in analogy to or according to methods that are known in the art.

The present invention relates also to pharmaceutical compositions that comprise a compound of formula (1), (2), (3) or (4) as active ingredient and that can be used in combination with tetracyclines in the treatment of infective diseases mentioned at the beginning. Compositions for enteral administration, such as nasal, buccal, rectal, uretal or, especially, oral administration to warm-blooded animals, especially humans, are preferred. The compositions comprise the active ingredient alone or, preferably, together with a pharmaceutically acceptable carrier. The dosage of the active ingredient depends upon the tetracycline used, the disease to be treated and upon the species, its age, weight, and individual condition, the individual pharmacokinetic data, and the mode of administration.

The present invention relates especially to pharmaceutical compositions that comprise a compound of formula (1), (2), (3) or (4), a tautomer or a pharmaceutically acceptable salt, or a hydrate or solvate thereof, and at least one pharmaceutically acceptable carrier.

The invention relates also to pharmaceutical compositions for use in combination with tetracyclines in a method for the prophylactic or especially therapeutic management of the human or animal body, in particular in a method of treating infective disease, especially those mentioned hereinabove.

The invention relates also to processes and to the use of compounds of formula (1), (2), (3) or (4) for the preparation of pharmaceutical preparations which comprise compounds of formula (1), (2), (3) or (4) as active component (active ingredient).

A pharmaceutical composition for the prophylactic or especially therapeutic management of an infective disease, of a warm-blooded animal, especially a human, comprising a novel compound of formula (1), (2), (3) or (4) as active ingredient in combination with a tetracycline in a quantity that is prophylactically or especially therapeutically active against the said infectious diseases, is likewise preferred. Preferred are pharmaceutical compositions suitable for oral administration.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from In in vitro tests, the compounds of formula (1), (2), (3) or (4) show specific activity in i) TetR/tetO interaction and binding experiments and in ii) microdilution assays with clinical patient isolates that are resistant to tetracyclines where combinations of compounds of formula (1), (2), (3) or (4) significantly reduce the MIC of tetracyclines (Table Experimental part).

Pharmaceutical compositions according to the invention are compositions for enteral administration, such as nasal, buccal, rectal or, especially, oral administration, and for parenteral administration, such as intravenous, intramuscular or subcutaneous administration. The compositions comprise the compound of formula (1), (2), (3) or (4) alone or mixed with the tetracycline, and preferably together with a pharmaceutically acceptable carrier. The dosage of the active ingredients depends upon the tetracycline used, the patient, its age, weight, and individual condition, the individual pharmacokinetic data, and the mode of administration.

The pharmaceutical compositions comprise from approximately 5% to approximately 95% of active ingredient(s). Single-dose administration forms comprise from approximately 20% to approximately 90% of the mentioned compound of formula (1), (2), (3) or (4), optionally in a mixture together with a tetracycline, and forms that are not of single-dose type from approximately 5% to approximately 20% of the mentioned compound or compound mixture. Unit dose forms are, for example, coated and uncoated tablets, ampoules, vials, suppositories, or capsules. Further dosage forms are, for example, ointments, creams, pastes, foams, tinctures, lip-sticks, drops, syrups, sprays, and the like. Examples are capsules containing from about 0.05 g to about 1.0 g of a mixture of the active ingredients.

It is possible to use the mixture of a compound of formula (1), (2), (3) or (4) with a tetracycline in two separate pharmaceutical unit dose forms, and such a combination is also part of the present invention.

The pharmaceutical compositions of the present invention are prepared in a manner known per se, for example by means of conventional mixing, granulating, coating, dissolving, emulsifying or lyophilizing processes. Optionally, the compounds can be formulated in liposomes.

For parenteral administration solutions of the active ingredients are preferred, and also suspensions, emulsions or dispersions, especially isotonic aqueous solutions, dispersions, emulsions or suspensions which, for example in the case of lyophilized compositions comprising the active ingredients alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms. The alcohol component of these fatty acid esters has a maximum of 6 carbon atoms and is a monovalent or polyvalent, for example a mono-, di- or trivalent, alcohol, especially glycol and glycerol. As mixtures of fatty acid esters, vegetable oils such as cottonseed oil, almond oil, olive oil, castor oil, sesame oil, soybean oil and groundnut oil are especially useful.

The manufacture of injectable preparations is usually carried out under sterile conditions, as is the filling, for example, into ampoules or vials, and the sealing of the containers.

Suitable carriers for oral compositions are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropyl-methylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved, emulsified or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

The present invention relates furthermore to a method for the treatment of bacterial infections, which comprises administering a compound of formula ((1), (2), (3) or (4) as defined hereinabove, and of a mixture of a compound of formula (1), (2), (3) or (4), and of tetracycline or of another member of the tetracycline family of antibiotics, such as minocycline, doxycycline and tigecycline, in a quantity effective against said disease, to a warm-blooded animal requiring such treatment. The mixture can be administered in the form of pharmaceutical compositions comprising the mixture, or also the components separately at the same time or at different times within the day, prophylactically or therapeutically, preferably in an amount effective against the specific disease, to a warm-blooded animal, for example a human, requiring such treatment. In the case of an individual having a bodyweight of about 70 kg the daily dose of the mixture administered is from approximately 0.5 g to approximately 5 g, preferably from approximately 0.05 g to approximately 2 g, of a mixture comprising from 5% to approximately 95% containing the components in relative amounts of between 1:1 up to 1:10'000, preferably 1:10 up to 1:5'000.

The following Examples serve to illustrate the invention without limiting the invention in its scope.

EXAMPLES

Liquid Chromatography (LC)

HPLC Column: Reverse Phase, Uptisphere Strategy C18-2, 5 μm 4.6×250 mm;

Wavelength: 254 nm or 280 nm; HPLC Apparatus Type: Agilent 1100 Series, DAD detector; MS Apparatus Type: Agilent MSD Trap XCT positive/negative mode switching, Ionization mode APCI.

LCMS System 01 (LCMS 01): Gradient 01

Solvent A: Water/methanol (95:5), 0.2% acetic acid; Solvent B: Methanol/water (95;5), 0.2% acetic acid;

| Time (min) | Flow (mL/min) | % A | % B |
|---|---|---|---|
| 0.00 | 1 | 100 | 0 |
| 10.00 | 1 | 0 | 100 |
| 18.00 | 1 | 0 | 100 |
| 18.10 | 1 | 100 | 0 |
| 20.00 | 1 | 100 | 0 |

Examples 1-3, 5-11 and 39-42, Compounds of Formula (1)

General Synthesis Scheme for Compounds of Formula (1)

Step 1

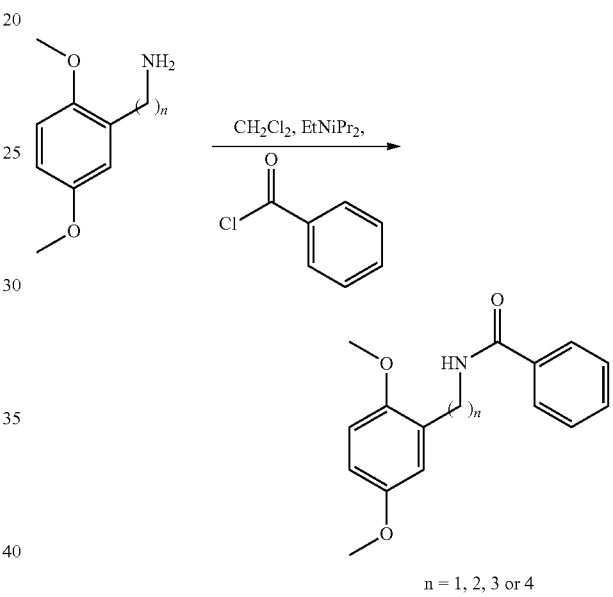

n = 1, 2, 3 or 4

To a magnetically stirred solution of 2,5-dimethoxybenzylamine (n=1) (500 mg, 2.99 mmol, 0.45 mL) in $CH_2Cl_2$ (4 mL) at room temperature was added drop wise benzoyl chloride (504 mg, 3.59 mmol, 0.42 mL) followed by ethyldiisopropylamine (0.5 mL). The mixture was stirred for a further 22.5 hours before being concentrated in vacuo. The residue was purified over silica gel with 0-50% ethyl acetate in cyclohexane to yield N-[(2,5-dimethoxyphenyl)methyl]benzamide (n=1) (728 mg, 2.68 mmol) in 90% yield.

Step 2

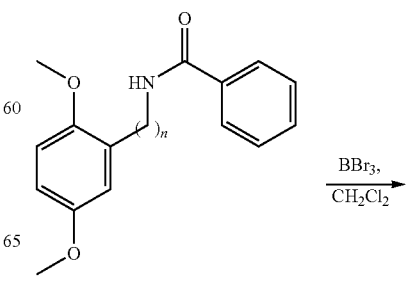

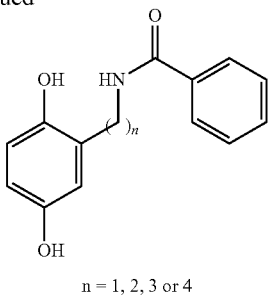

n = 1, 2, 3 or 4

To a magnetically stirred solution of N-[(2,5-dimethoxyphenyl)methyl]benzamide (n=1) (563 mg, 2.08 mmol) in $CH_2Cl_2$ at room temperature was added drop wise boron tribromide (2.08 g, 8.30 mmol, 0.80 mL) and stirred for a further 21 hours before being quenched cautiously with MeOH (4 mL). The reaction mixture was then concentrated in vacuo and further portions of MeOH (5×4 mL) were added and concentrated in sequence. The residue was purified over silica gel with 0-100% EtOAc in cyclohexane to yield N-[(2,5-dihydroxyphenyl)methyl]benzamide (n=1, Example 1) (450 mg, 1.85 mmol) in 89% yield. LCMS ESL 244.0 $(M+H)^+$, $R_t$ 7.5 min (LCMS 01).

General Synthesis Scheme for Compounds of Formula (2)

Synthetic Scheme for Example 4, 43 and 44
Step 1

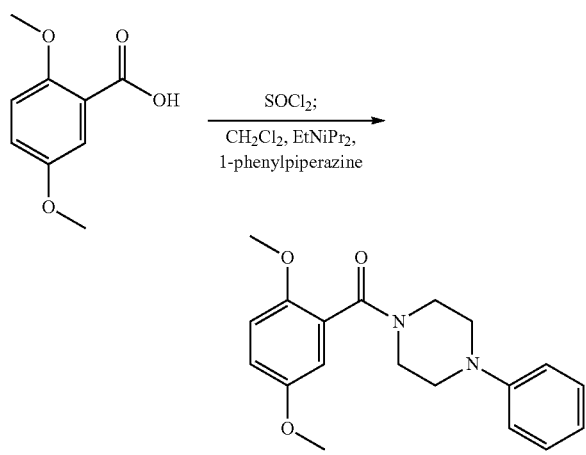

A solution of 2,5-dimethoxybenzoic acid (100 mg, 0.549 mmol) in $SOCl_2$ (1 mL) at 75° C. was stirred magnetically for 1 h, then cooled and concentrated in vacuo to remove excess thionylchloride. To a mixture of this acid chloride in 1 mL $CH_2Cl_2$ was added drop wise 1-phenylpiperazine (89 mg, 0.549 mmol, 120 µL) solution in 1 mL $CH_2Cl_2$ followed by ethyldiisopropylamine (0.2 mL). The mixture was stirred for a further 18.5 hours before being concentrated in vacuo. The residue was purified over silica gel with 0-100% ethyl acetate in cyclohexane to yield (2,5-dimethoxyphenyl)-(4-phenylpiperazin-1-yl)methanone (170 mg, 0.521 mmol) in 95% yield.

Step 2

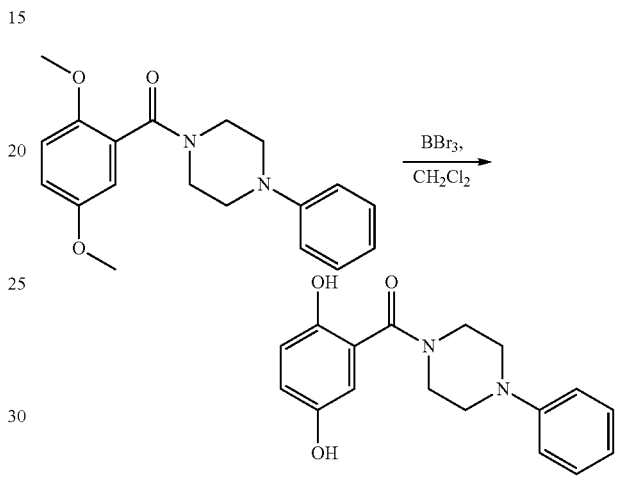

To a magnetically stirred solution of (2,5-dimethoxyphenyl)-(4-phenylpiperazin-1-yl)-methanone (160 mg, 0.490 mmol) in $CH_2Cl_2$ (8 mL) at 0° C. was added drop wise boron tribromide (246 g, 0.980 mmol, 93 µL) and stirred at room temperature for a further 20 hours before being quenched cautiously with MeOH (4 mL). The reaction mixture was then concentrated in vacuo and further portions of MeOH (4×7 mL) were added and concentrated in sequence. The residue was purified over silica gel with 0-100% EtOAc in cyclohexane, and semi-preperative HPLC with 50 to 95% MeOH in $H_2O$ to yield N-[(2,5-dihydroxyphenyl)methyl]benzamide (15 mg, 0.050 mmol), Example 4, in 10% yield. LCMS ESL 299 $[M+H]^+$, $ESI^-$: 297 $[M-H]^-$, $R_t$ 11.0 min (LCMS 01).

| Example | Structure | Exact mass (g/mol) | $R_t$ (min) | m/z |
|---|---|---|---|---|
| 1 | 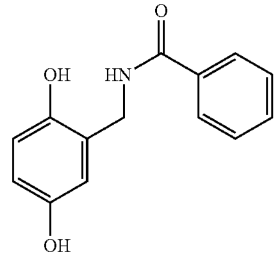 [SMILES: O=C(NCc1cc(O)ccc1O)c1ccccc1] | 243.09 | 7.5 | 244 $[M + H]^+$ |

-continued

| Example | Structure | Exact mass (g/mol) | R$_t$ (min) | m/z |
|---|---|---|---|---|
| 2 | 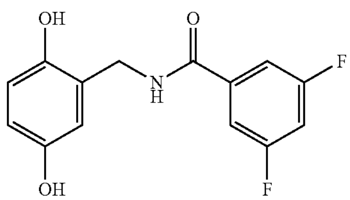 [SMILES: O=C(NCc1cc(O)ccc1O)c1cc(F)cc(F)c1] | 279.07 | 11.0 | 280 [M + H]$^+$ |
| 3 | 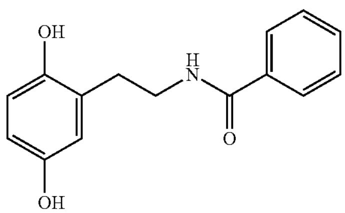 [SMILES: O=C(NCCc1cc(O)ccc1O)c1ccccc1] | 257.11 | 9.9 | 258 [M + H]$^+$ |
| 4 | 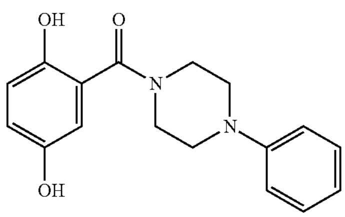 [SMILES: O=C(c1cc(O)ccc1O)N1CCN(c2ccccc2)CC1] | 298.13 | 11.0 | 299 [M + H]$^+$<br>297 [M − H]$^−$ |
| 5 | 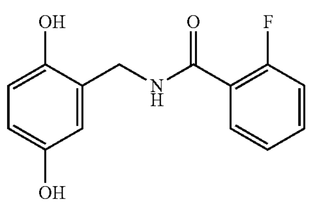 [SMILES: O=C(NCc1cc(O)ccc1O)c1ccccc1F] | 261.08 | 9.9 | 259 [M − H]$^−$ |
| 6 | 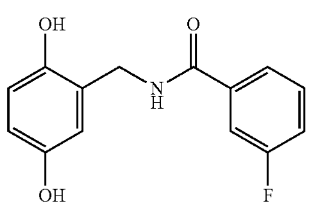 [SMILES: O=C(NCc1cc(O)ccc1O)c1cccc(F)c1] | 261.08 | 10.4 | 260 [M − H]$^−$ |
| 7 | 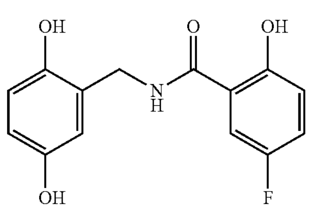 [SMILES: O=C(NCc1cc(O)ccc1O)c1cc(F)ccc1O] | 277.08 | 10.8 | 278 [M + H]$^+$<br>276 [M − H]$^−$ |
| 8 | 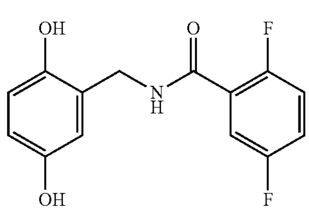 [SMILES: O=C(NCc1cc(O)ccc1O)c1cc(F)ccc1F] | 279.07 | 10.2 | 280 [M + H]$^+$<br>278 [M − H]$^−$ |

-continued
| Example | Structure | Exact mass (g/mol) | R$_t$ (min) | m/z |
|---|---|---|---|---|
| 9 | 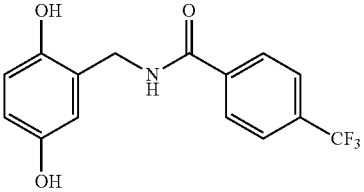 [SMILES: O=C(NCc1cc(O)ccc1O)c1ccc(C(F)(F)F)cc1] | 311.08 | 11.7 | 312 [M + H]$^+$<br>310 [M − H]$^−$ |
| 10 | 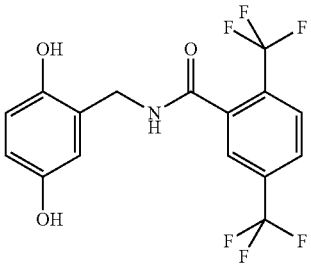 [SMILES: O=C(NCc1cc(O)ccc1O)c1cc(C(F)(F)F)ccc1C(F)(F)F] | 379.06 | 11.4 | 380 [M + H]$^+$<br>378 [M − H]$^−$ |
| 11 | 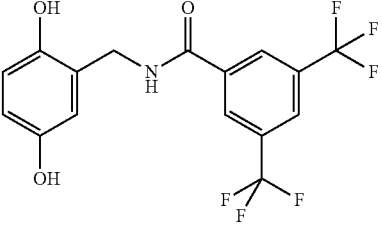 [SMILES: O=C(NCc1cc(O)ccc1O)c1cc(C(F)(F)F)cc(C(F)(F)F)c1] | 379.06 | 12.7 | 380 [M + H]$^+$<br>378 [M − H]$^−$ |
| 39 | 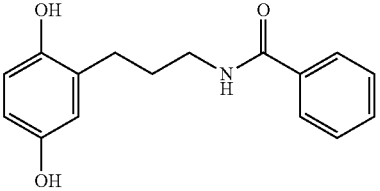 [SMILES: O=C(NCCCc1cc(O)ccc1O)c1ccccc1] | 271.12 | 10.34 | 272 [M + H]$^+$<br>270 [M − H]$^−$ |
| 40 | 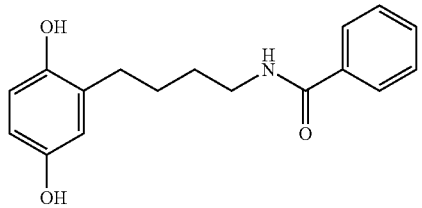 [SMILES: O=C(NCCCCc1cc(O)ccc1O)c1ccccc1] | 285.14 | 10.45 | 286 [M + H]$^+$ |
| 41 | 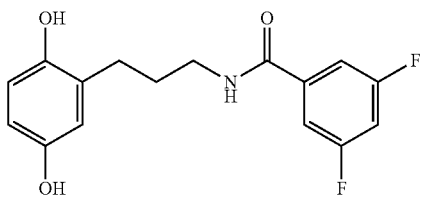 [SMILES: O=C(NCCCc1cc(O)ccc1O)c1cc(F)cc(F)c1] | 307.10 | 11.23 | 308 [M + H]$^+$<br>306 [M − H]$^−$ |

| Example | Structure | Exact mass (g/mol) | $R_t$ (min) | m/z |
|---|---|---|---|---|
| 42 | 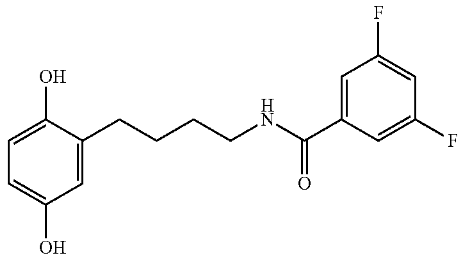 [SMILES: O=C(NCCCCc1cc(O)ccc1O)c1cc(F)cc(F)c1] | 321.12 | 11.38 | 322 [M + H]$^+$<br>320 [M − H]$^-$ |
| 43 | 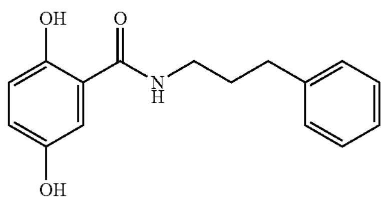 [SMILES: O=C(NCCCc1ccccc1)c1cc(O)ccc1O] | 271.12 | 12.35 | 272 [M + H]$^+$<br>270 [M − H]$^-$ |
| 44 | 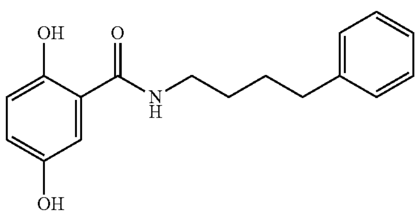 [SMILES: O=C(NCCCCc1ccccc1)c1cc(O)ccc1O] | 285.14 | 12.78 | 286 [M + H]$^+$<br>284 [M − H]$^-$ |

Examples 12, 13 and 17, Compound of Formula (3)

General Synthesis Scheme
Step 1

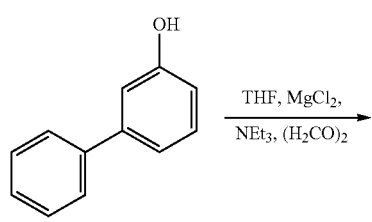

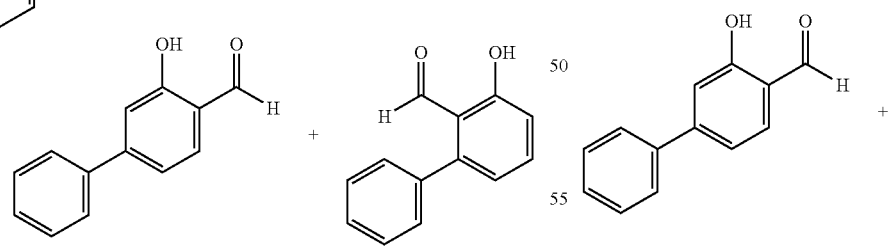

To a magnetically stirred solution of 3-phenylphenol (457 mg, 2.69 mmol) in tetrahydrofuran (30 mL) at room temperature was added magnesium chloride (511 mg, 5.37 mmol), triethylamine (543 mg, 5.37 mmol, 0.75 mL), and then paraformaldehyde (242 mg, 8.06 mmol). The reaction mixture was heated to 66° C. and stirred for 4 days, cooled to room temperature and the solvents removed in vacuo. The residue was partitioned between H$_2$O (50 mL) and CH$_2$Cl$_2$ (50 mL), and the layers shaken and separated. The aqueous layer was extracted with CH$_2$Cl$_2$ (2×50 mL), and the combined organic extracts were washed with brine (50 mL), dried (Na$_2$SO$_4$) and concentrated in vacuo. The residue was purified over silica gel with 0-30% ethyl acetate in cyclohexane to yield an approximate 1:1 inseparable mixture of 2-hydroxy-4-phenylbenzaldehyde and 2-hydroxy-6-phenylbenzaldehyde (300 mg, 1.51 mmol) in 56% yield.

Step 2

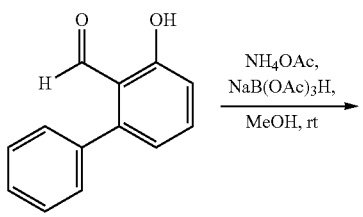

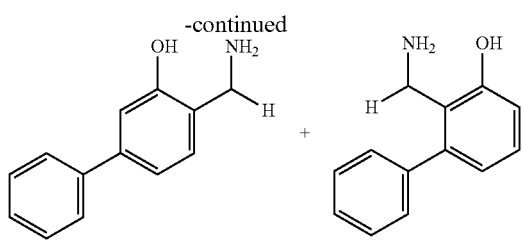

A solution of 2-hydroxy-4-phenylbenzaldehyde/2-hydroxy-6-phenylbenzaldehyde (300 mg, 1.51 mmol) and ammonium acetate (1.28 g, 16.65 mmol) in methanol (20 mL) was stirred magnetically at room temperature for 1 hour. To the mixture was added sodium triacetoxy-borohydride (642 mg, 3.03 mmol) and stirred at room temperature for a further 18 hours. The reaction was quenched by slow addition of 1N aqueous hydrochloric acid and adjusted to pH 2. The mixture was concentrated in vacuo, and the residue dissolved in CH$_2$Cl$_2$ (50 mL) and adjusted to pH 12 with 4N NaOH. The layers were shaken and separated, and the aqueous layer extracted with CH$_2$Cl$_2$ (3×40 mL). The combined organic phases were dried (Na$_2$SO$_4$) and concentrated in vacuo. The residue was purified over silica gel with 0-20% MeOH in CH$_2$Cl$_2$ to yield an approximate 1:1 inseparable mixture of 2-(aminomethyl)-3-phenylphenol and 2-(aminomethyl)-5-phenylphenol in 13% yield.

Step 3

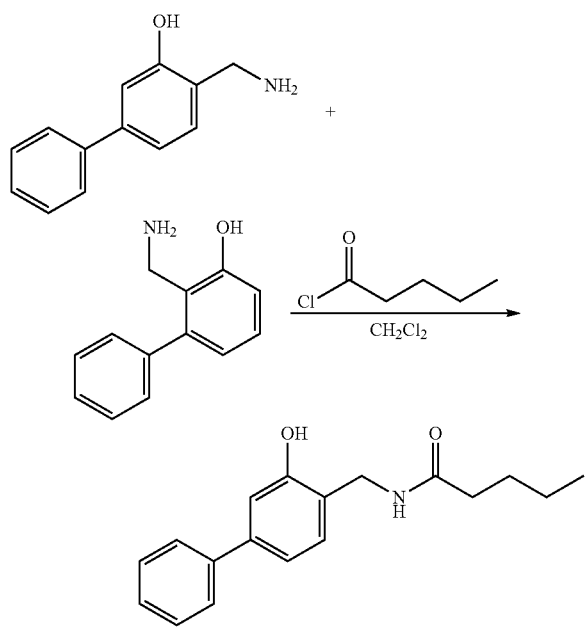

To a magnetically stirred solution of 2-(aminomethyl)-3-phenylphenol/2-(aminomethyl)-5-phenylphenol (40 mg, 0.20 mmol) in CH$_2$Cl$_2$ (1 mL) at room temperature was added dropwise pentanoylchloride (29 mg, 0.24 mmol, 29 μL) followed several minutes later by ethyldiisopropylamine (0.1 mL). The reaction was stirred at room temperature for a further 18.5 hours, quenched with H$_2$O (10 mL) and partitioned with CH$_2$Cl$_2$ (10 mL). The aqueous layer was extracted with CH$_2$Cl$_2$ (10 mL), and the combined organic extracts were dried (Na$_2$SO$_4$), filtered and concentrated in vacuo. The residue was purified over silica gel with 0-30% ethyl acetate in cyclohexane to yield N-[(2-hydroxy-4-phenyl-phenyl)-methyl]pentanamide (13 mg, 0.05 mmol), Example 12, in 24% yield as the only isolated product. LCMS ESL 284 [M+H]$^+$, R$_t$ 8.9 min (LCMS 01)

Examples 14-16, Compound of Formula (3)

General Synthesis Scheme

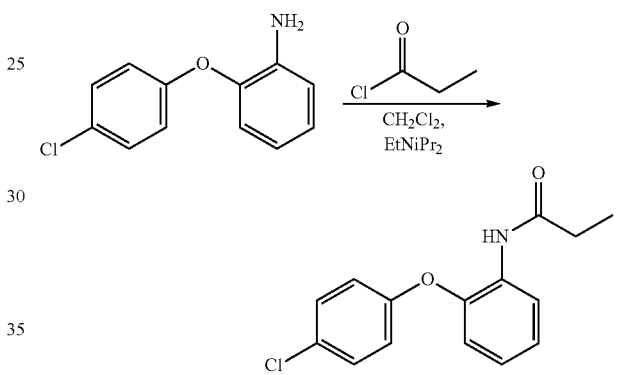

To a magnetically stirred solution of 2-(4-chlorophenoxy) aniline (95 mg, 0.432 mmol, 76 μL) in CH$_2$Cl$_2$ (1.5 mL) at room temperature was added dropwise propionylchloride (48 mg, 0.518 mmol, 45 μL) followed several minutes later by ethyldiisopropylamine (0.2 mL). The reaction was stirred at room temperature for a further 17 hours, quenched with H$_2$O (10 mL) and partitioned with CH$_2$Cl$_2$ (10 mL). The aqueous layer was extracted with CH$_2$Cl$_2$ (10 mL), and the combined organic extracts were dried (Na$_2$SO$_4$), filtered and concentrated in vacuo. The residue was purified over silica gel with 0-50% ethyl acetate in cyclohexane to yield N-[2-(4-chlorophenoxyl)phenyl]propanamide (109 mg, 0.395 mmol), Example 14, in 91% yield. LCMS ESL 276 [M+H]$^+$, R$_t$ 9.1 min (LCMS 01).

| Example | Structure | Exact mass (g/mol) | R$_t$ (min) | m/z |
|---|---|---|---|---|
| 12 | 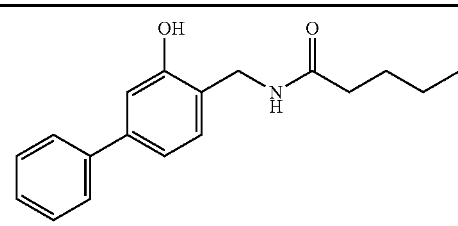 | 283.16 | 8.9 | 284 [M + H]$^+$ |

| Example | Structure | Exact mass (g/mol) | $R_t$ (min) | m/z |
|---|---|---|---|---|
| 13 | 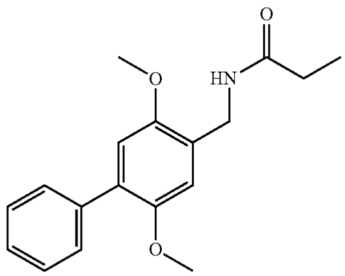 [SMILES: CCC(=O)NCc1cc(OC)c(-c2ccccc2)cc1OC] | 299.15 | 9.3 | 300 [M + H]$^+$ |
| 14 | 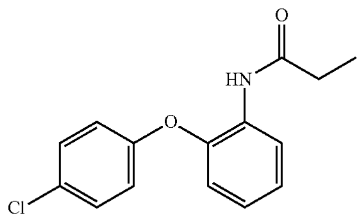 [SMILES: CCC(=O)Nc1ccccc1Oc1ccc(Cl)cc1] | 275.07 | 9.1 | 276 [M + H]$^+$ |
| 15 | 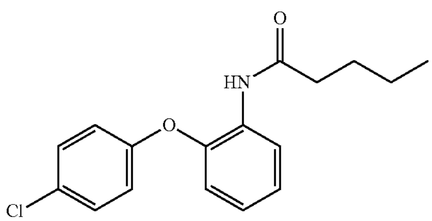 [SMILES: CCCCC(=O)Nc1ccccc1Oc1ccc(Cl)cc1] | 303.10 | 9.4 | 304 [M + H]$^+$ |
| 16 | 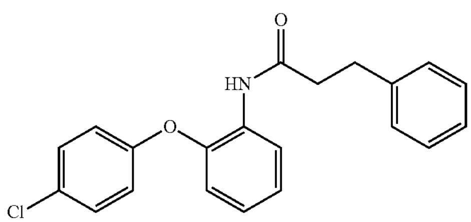 [SMILES: O=C(CCc1ccccc1)Nc1ccccc1Oc1ccc(Cl)cc1] | 351.10 | 9.5 | 352 [M + H]$^+$ |
| 17 | 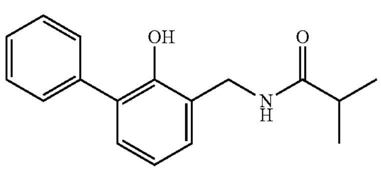 [SMILES: CC(C)C(=O)NCc1cccc(-c2ccccc2)c1O] | 269.14 | 8.9 | 270 [M + H]$^+$ |

Examples 18-19, 21-38, Compound of Formula (4)
General Synthesis Scheme
Step 1

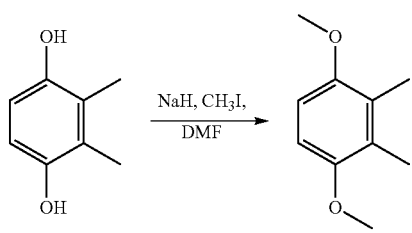

To a magnetically stirred solution of 2,3-dimethylhydroquinone (8.60 g, 62.3 mmol) in dry DMF (100 mL) at 0° C. and protecting gas (argon) was added sodium hydride (10.26 g, 256 mmol) in one portion followed by methyl iodide (21.47 g, 151 mmol, 9.4 mL) over a period of 40 minutes at −5° C. The reaction was stirred for a further 3.5 hours before being quenched at 0° C. with H$_2$O (150 mL). The reaction mixture was stirred for further 20 minutes, and the precipitate was filtered off, washed with H$_2$O and dried at 40° C. in vacuo. The solid was dissolved in methanol (60 mL) at 70° C. and cooled to room temperature while stirring, and the precipitation was filtered off, washed with cold methanol and dried to yield 1,4-dimethoxy-2,3-dimethyl-benzene (9.86 g, 59.3 mmol) in 95% yield.

Step 2

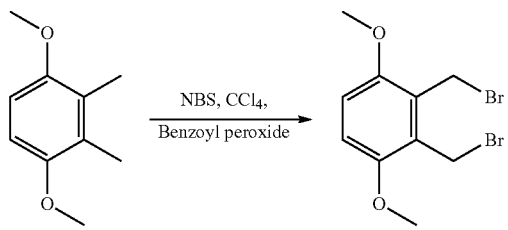

To a magnetically stirred solution of 1,4-dimethoxy-2,3-dimethyl-benzene (13.90 g, 83.6 mmol) in carbon tetrachloride (300 mL) at room temperature was added N-bromosuccinimide (32.2 g, 176 mmol) in one portion, and the reaction mixture was heated up to 65° C. Benzoyl peroxide (0.54 g, 2.23 mmol) was added at 65° C., and the reaction mixture stirred for further 4 hours before cooling down to 55° C. The reaction mixture was filtered, the solid washed with carbon tetrachloride, and the combined filtrates were concentrated in vacuo to yield 2,3-bis(bromomethyl)-1,4-dimethoxy-benzene (26.8 g, 82.7 mmol) in 99% yield.

Step 3

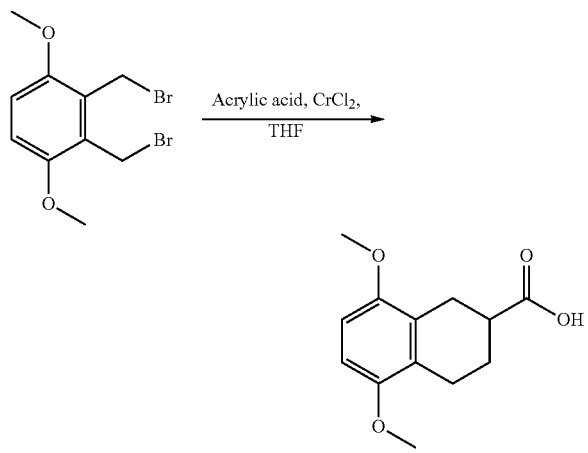

To a magnetically stirred solution of 2,3-bis(bromomethyl)-1,4-dimethoxy-benzene (26.8 g, 82.7 mmol) in tetrahydrofuran (500 mL) at room temperature was added acrylic acid (28.61 g, 397 mmol, 27.2 ml) in one portion, and the reaction mixture was cooled down to 0° C. Chromium(II) chloride was added in small portions over a period of 2 hours, and the reaction mixture was stirred for 15.5 hours at room temperature. The reaction mixture was concentrated in vacuo to 150 mL, filtered, and the filtrate was quenched with $H_2O$ (250 mL). The aqueous layer was extracted with ethyl acetate: cyclohexane 1:2, (3×250 mL), and the combined organic extracts were washed with brine (100 mL), dried ($Na_2SO_4$) and concentrated in vacuo. The residue was taken up in ethyl acetate (50 mL), and the precipitation was filtered off, washed with ethyl acetate until the filtrate was clear and colourless, and then dried in vacuo at 40° C. to yield 5,8-dimethoxytetralin-2-carboxylic acid (6.46 g, 27.3 mmol) in 41% yield.

Step 4

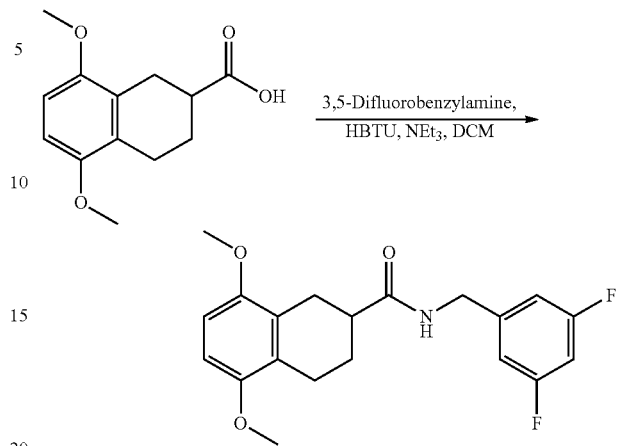

A mixture of 5,8-dimethoxytetralin-2-carboxylic acid (2.00 g, 8.46 mmol), 3,5-difluoro-benzylamine (0.74 g, 5.17 mmol, 1.8 mL), triethylamine (2.57 g, 25.4 mmol, 3.52 mL) and HBTU (3.53 g, 9.31 mmol) in $CH_2Cl_2$ (90 mL) was stirred magnetically at room temperature and under nitrogen atmosphere for 19 hours before being diluted with $CH_2Cl_2$ (100 mL). The organic phase was washed with 20% aq. $K_2CO_3$ (3×80 mL), 10% aq. citric acid (80 mL), $H_2O$ (2×80 mL), brine (80 mL), dried ($Na_2SO_4$) and concentrated in vacuo. The residue was dissolved in $CH_2Cl_2$ (250 mL), washed with $H_2O$ (3×100 mL), brine (100 mL), dried ($Na_2SO_4$) and concentrated in vacuo to yield N-[(3,5-difluorophenyl)-methyl]-5,8-dimethoxy-tetralin-2-carboxamide (2.95 g, 8.16 mmol) in 95% yield.

Step 5

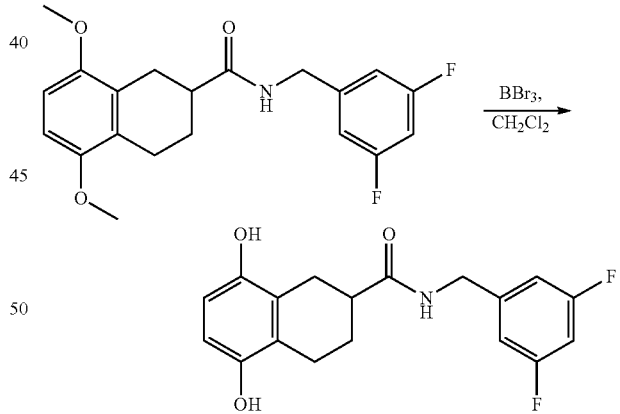

To a magnetically stirred solution of N-[(3,5-difluorophenyl)methyl]-5,8-dimethoxy-tetralin-2-carboxamide (160 mg, 0.443 mmol) in $CH_2Cl_2$ (10 mL) at −10° C. was added drop wise boron tribromide (221.8 mg, 0.885 mmol, 0.08 mL), and the mixture stirred for 15 minutes below −5° C. and a further 17 hours at room temperature before being quenched cautiously at 0° C. with MeOH (10 mL). The reaction mixture was then concentrated in vacuo, and further portions of MeOH (7×10 mL) were added and concentrated in sequence. The residue was dissolved in MeOH (2 mL), $H_2O$ (60 mL) was added and the aqueous layer was extracted with ethyl acetate (3×40 mL), the combined organic phases washed with H₂O (40 mL), brine (40 mL), dried (Na₂SO₄) and concentrated in vacuo. The residue was purified over RP-C18 with 5-95% MeOH in H₂O to yield N-[(3,5-difluorophenyl)methyl]-5,8-dihydroxy-tetralin-2-carboxamide (35 mg, 105.0 mmol), Example 23, in 24% yield. LCMS ESL 334 [M+H]⁺, 332 [M+H]⁻, $R_f$ 11.0 min (LCMS 01)

Synthetic Scheme for Example 20

Step 1

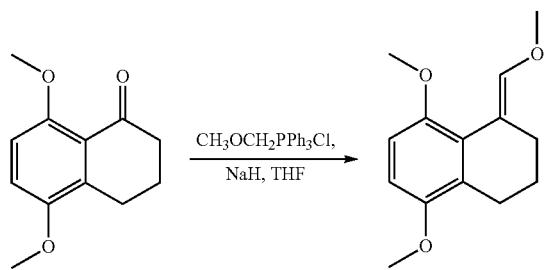 [SMILES: COc1ccc(OC)c2c1CCCC2=O ; CO/C=C1\CCCc2c(OC)ccc(OC)c21]

To a magnetically stirred mixture of (methoxymethyl)triphenylphosphonium chloride (3.14 g, 9.07 mmol) in THF (100 mL) at room temperature was added NaH (490 mg, 12.36 mmol) and stirred at room temperature for 15 minutes. To the reaction was added 5,8-dimethoxytetralin-1-one (1.70 g, 8.24 mmol) in THF (40 mL) and stirred at room temperature for 30 minutes, then at reflux under nitrogen atmosphere for 15 hours, cooled to room temperature, and ethanol (80 mL) added. Aqueous ammonium chloride solution (80 mL) was added, the mixture extracted with ethyl acetate (3×80 mL), and the extracts washed with H₂O (2×60 mL), brine (70 mL), dried (Na₂SO4) and concentrated in vacuo. The residue was purified over silica gel with 0-100% ethyl acetate in cyclohexane to yield 5,8-dimethoxytetralin-1-carbaldehyde (1.54 g, 6.57 mmol) in 80% yield.

Step 2

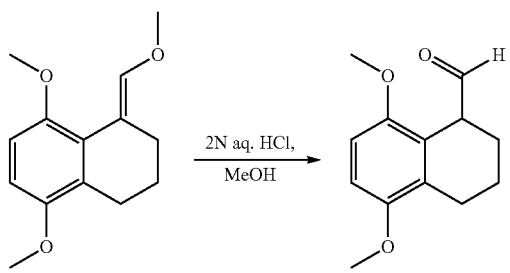 [SMILES: "MeOH" ; CO/C=C1\CCCc2c(OC)ccc(OC)c21 ; COc1ccc(OC)c2c1CCCC2C=O]

To a magnetically stirred mixture of (1E)-5,8-dimethoxy-1-(methoxymethylene)tetralin (1.54 g, 6.57 mmol) in MeOH (15 mL) was added 2 N aq. HCl (77 mL) and stirred at reflux under nitrogen atmosphere for 15 hours, cooled to room temperature and MeOH removed in vacuo. The residue was extracted with CH₂Cl₂ (2×100 mL), dried (Na₂SO4) and concentrated in vacuo. The residue was purified over silica gel with 0-100% ethyl acetate in cyclohexane to yield 5,8-dimethoxytetralin-1-carbaldehyde (1.21 g, 5.49 mmol) in 84% yield.

Step 3

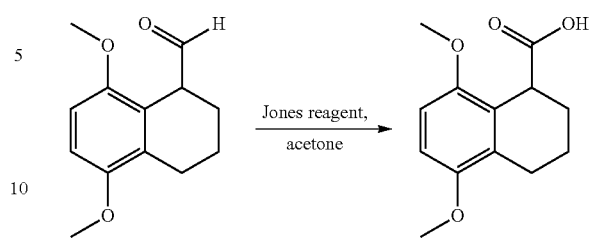

To a magnetically stirred mixture of 5,8-dimethoxytetralin-1-carbaldehyde (1.21 g, 5.49 mmol) in acetone (12 mL) at 0° C. was added Jones reagent (1 mL) and stirred at room temperature under nitrogen atmosphere for 1 hour before being diluted with CH₂Cl₂ (50 mL). The solution was washed with 4% aq. NaOH (2×30 mL) and extracted with ethyl acetate (50 mL). The aqueous phase was acidified with 2 N HCl, extracted with CH₂Cl₂ (3×50 mL), washed with brine (50 mL), dried (Na₂SO4) and concentrated in vacuo to yield 5,8-dimethoxytetralin-1-carboxylic acid (250 mg, 1.06 mmol) in 19% yield.

Step 4

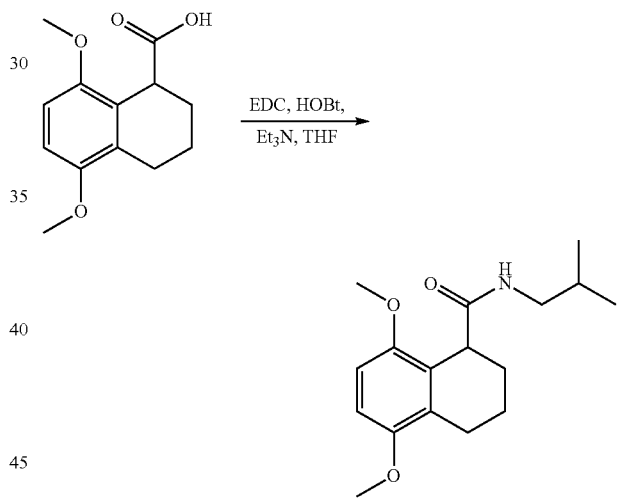

To a mixture of 5,8-dimethoxytetralin-1-carboxylic acid (100 mg, 0.423 mmol) and isobutylamine (31 mg, 0.423 mmol) in THF (5 mL) was added EDC (162 mg, 0.847 mmol), HOBt (68 mg, 0.508 mmol) and triethylamine (86 mg, 0.847 mmol, 118 μL) and stirred magnetically at room temperature under nitrogen atmosphere for 15 hours before being quenched with 10% aq. citric acid (10 mL). The mixture was extracted with ethyl acetate (3×8 mL), combined organic extracts were washed with 10% aq. citric acid (2×7 mL), sat. aq. NaHCO₃ (3×8 mL), H₂O (2×8 mL), dried (Na₂SO4) and concentrated in vacuo. The residue was purified over silica gel with 0-100% ethyl acetate in cyclohexane, and with semi-preparative HPLC with 50 to 95% MeOH in H₂O to yield N-isobutyl-5,8-dimethoxy-tetralin-1-carboxamide (14 mg, 0.048 mmol), Example 20, in 11% yield.

| Example | Structure | Exact mass (g/mol) | R$_t$ (min) | m/z |
|---|---|---|---|---|
| 18 | 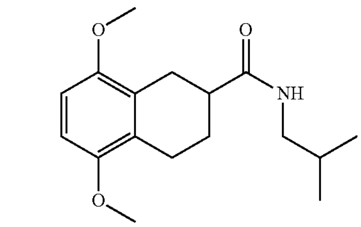 [SMILES: COc1ccc(OC)c2c1CCC(C(=O)NCC(C)C)C2] | 291.18 | 13.0 | 292 [M + H]$^+$ |
| 19 | 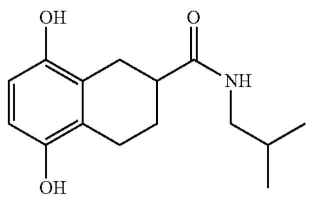 [SMILES: CC(C)CNC(=O)C1CCc2c(O)ccc(O)c2C1] | 263.15 | 7.7 | 264 [M + H]$^+$ |
| 20 | 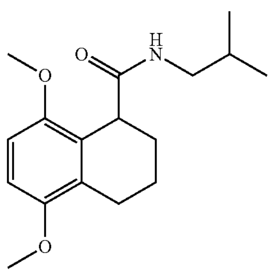 [SMILES: COc1ccc(OC)c2c1CCCC2C(=O)NCC(C)C] | 291.18 | 13.1 | 292 [M + H]$^+$ |
| 21 | 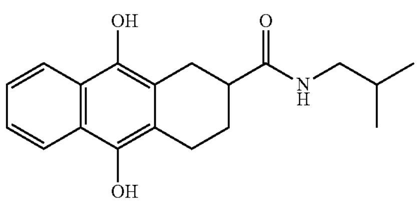 [SMILES: CC(C)CNC(=O)C1CCc2c(c(O)c3ccccc3c2O)C1] | 313.17 | 12.9 | 312 [M − H]$^-$ |
| 22 | 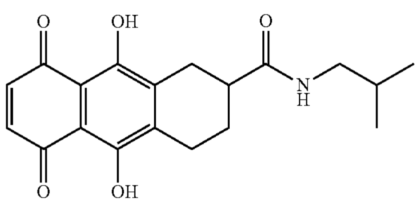 [SMILES: CC(C)CNC(=O)C1CCc2c(O)c3c(c(O)c2C1)C(=O)C=CC3=O] | 343.14 | 13.7 | 344 [M + H]$^+$ |
| 23 | 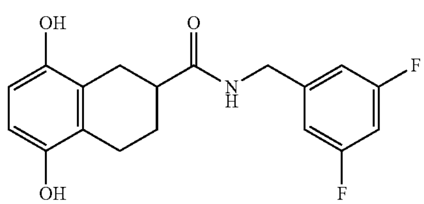 [SMILES: O=C(NCc1cc(F)cc(F)c1)C1CCc2c(O)ccc(O)c2C1] | 333.12 | 11.0 | 334 [M + H]$^+$ 332 [M − H]$^-$ |
| 24 | 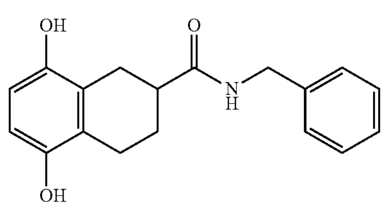 [SMILES: O=C(NCc1ccccc1)C1CCc2c(O)ccc(O)c2C1] | 297.14 | 10.4 | 298 [M + H]$^+$ 296 [M − H]$^-$ |

-continued
| Example | Structure | Exact mass (g/mol) | R_t (min) | m/z |
|---|---|---|---|---|
| 25 | 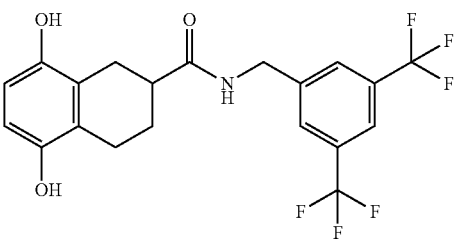 [SMILES: O=C(NCc1cc(C(F)(F)F)cc(C(F)(F)F)c1)C1CCc2c(O)ccc(O)c2C1] | 433.11 | 12.5 | 434 [M + H]+ 432 [M − H]− |
| 26 | 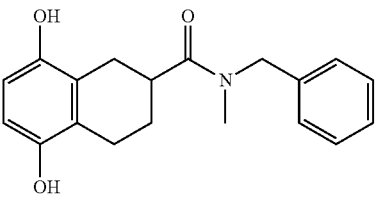 [SMILES: CN(Cc1ccccc1)C(=O)C1CCc2c(O)ccc(O)c2C1] | 311.15 | 11.2 | 312 [M + H]+ |
| 27 | 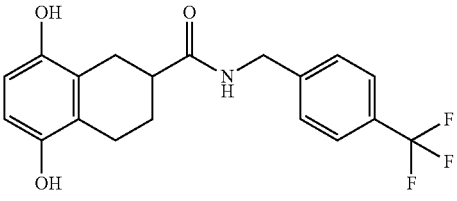 [SMILES: O=C(NCc1ccc(C(F)(F)F)cc1)C1CCc2c(O)ccc(O)c2C1] | 365.12 | 11.7 | 366 [M + H]+ 364 [M − H]− |
| 28 | 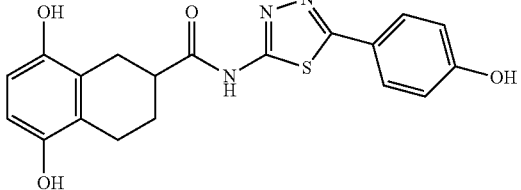 | 383.09 | 10.7 | 384 [M + H]+ 382 [M − H]− |
| 29 | 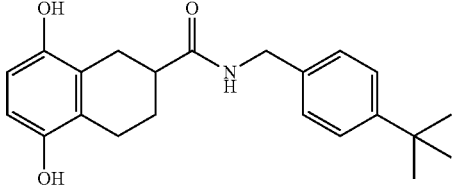 [SMILES: CC(C)(C)c1ccc(CNC(=O)C2CCc3c(O)ccc(O)c3C2)cc1] | 353.20 | 12.6 | 354 [M + H]+ 352 [M − H]− |
| 30 | 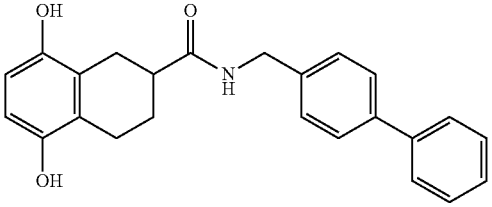 [SMILES: O=C(NCc1ccc(-c2ccccc2)cc1)C1CCc2c(O)ccc(O)c2C1] | 373.17 | | |
| 31 | 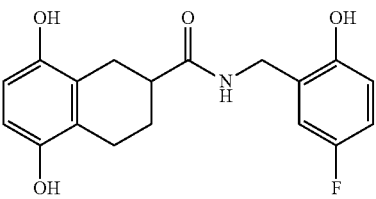 [SMILES: O=C(NCc1cc(F)ccc1O)C1CCc2c(O)ccc(O)c2C1] | 331.12 | 10.2 | 332 [M + H]+ 330 [M − H]− |

-continued

| Example | Structure | Exact mass (g/mol) | R$_t$ (min) | m/z |
|---|---|---|---|---|
| 32 | 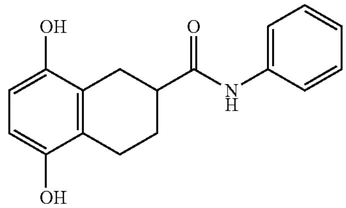 [SMILES: O=C(Nc1ccccc1)C1CCc2c(O)ccc(O)c2C1] | 283.12 | 10.5 | 284 [M + H]$^+$ 282 [M − H]$^-$ |
| 33 | 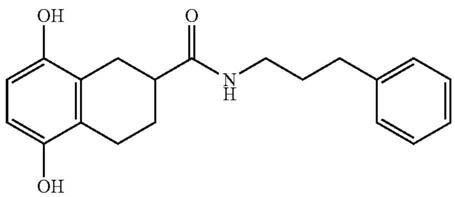 [SMILES: O=C(NCCCc1ccccc1)C1CCc2c(O)ccc(O)c2C1] | 325.17 | 8.5 | 326 [M + H]$^+$ |
| 34 | 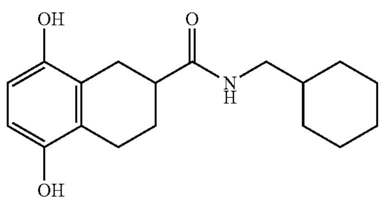 [SMILES: O=C(NCC1CCCCC1)C1CCc2c(O)ccc(O)c2C1] | 303.18 | 8.7 | 304 [M + H]$^+$ |
| 35 | 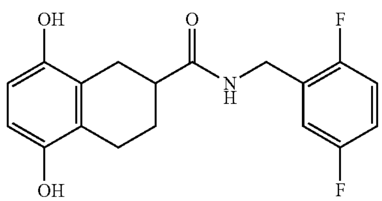 [SMILES: O=C(NCc1cc(F)ccc1F)C1CCc2c(O)ccc(O)c2C1] | 33.12 | 7.7 | 334 [M + H]$^+$ |
| 36 | 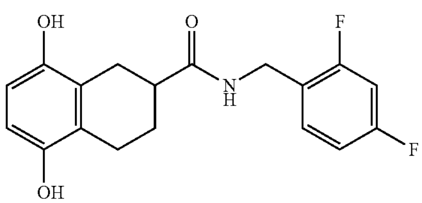 [SMILES: O=C(NCc1ccc(F)cc1F)C1CCc2c(O)ccc(O)c2C1] | 333.12 | 7.7 | 334 [M + H]$^+$ |
| 37 | 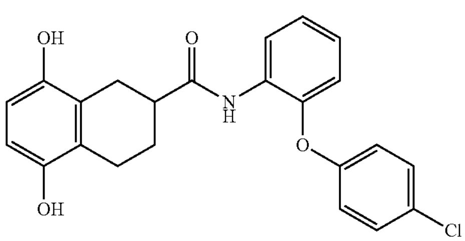 [SMILES: O=C(Nc1ccccc1Oc1ccc(Cl)cc1)C1CCc2c(O)ccc(O)c2C1] | 409.11 | 12.6 | 410 [M + H]$^+$ 408 [M − H]$^-$ |
| 38 | 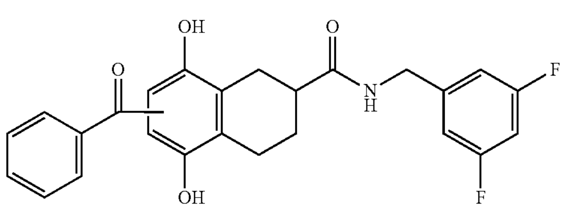 | 437.14 | 13.0 | 438 [M + H]$^+$ 436 [M − H]$^-$ |

Biacore Based DNA/Protein (tetO/TetR) Interaction Assay
FortéBio's Octet Method

The FortéBio technology (FortéBio, Inc., Menlo Park, Calif., USA) is a novel label-free methodology for analyzing macromolecular ligand/capture interactions. The Octet system can be used to measure real-time, label-free analysis of biomolecular interactions and provide information on affinity, kinetics and concentration. The instrument is designed to assay up to eight samples in parallel in 2 min from a standard 96-well micro-plate. The detection technology utilized in the Octet is based on Biolayer Interferometry (BLI). BLI relies on the reflective property of white light and is implemented in the Octet via the use of fiber optic-based biosensors. The biosensors are coated with molecules chosen to capture the targeted ligands. The measurements were performed on an Octet Red system equipped with streptavidin biosensor tips (SA). Tips were purchased from FortéBio.

Interaction Studies: FortéBio's Octet Red

Interaction analyses were conducted at 30° C. in running buffer (HBS-P+5 mmol/L $MgSO_4$) unless stated otherwise. (HBS-P buffer: 10 mM Hepes (pH 7.4), 150 mM NaCl, 0.005% (v/v) polysorbate P20, and 5 mmol/L $MgSO_4$; a 10×HBS-P buffer from GE Healthcare was used). Temperature control on the Octet was accomplished by holding the instrument at room temperature so that it could be heated to 30° C. Sensor tips were pre-wet for 10 min in running buffer immediately prior to use, and the micro plates used in the Octet were filled with 200 µl of sample or buffer per well and agitated at 600 rpm. For the experiments commercially available precoated streptavidine tips were used (SA).

Biotinylated oligos were loaded onto the FortéBio SA fibers in HBS-P buffer pH 7.4. Protein binding experiments were run with HBS-P buffer unless stated otherwise. After each run the tip was regenerated (maximum 4 times) with running buffer containing 0.3% w/v sodium dodecylsulfate (SDS).

Assay Setup

| Step No. | Step | Time s | Speed rpm | Remarks |
|---|---|---|---|---|
| 1 | Baseline | 180 | 1000 | Running buffer |
| 2 | Loading TetO | 900 | 600 | 50 nM in Running buffer |
| 3 | Baseline TetO | 180 | 600 | Running buffer |
| 4 | Association TetR | 420 | 600 | 1 µg/mL in Running buffer |
| 5 | Dissociation TetR | 240 | 600 | Running buffer |
| 6 | Displacement Comp/TC | 600 | 600 | Compound 10 µg/mL & Tetracycline 10 ng/mL mix in Running Buffer |
| 7 | Baseline Comp/TC | 180 | 600 | Running buffer |
| 8 | Regeneration Step 1 | 5 | 1000 | Running buffer & 0.3% SDS |
| 9 | Regeneration Step 2 | 5 | 1000 | Running buffer |
| 10 | Regeneration Step 1 | 5 | 1000 | Running buffer & 0.3% SDS |
| 11 | Regeneration Step 2 | 5 | 1000 | Running buffer |
| 12 | Regeneration Step 1 | 5 | 1000 | Running buffer & 0.3% SDS |
| 13 | Regeneration Step 2 | 5 | 1000 | Running buffer |
| Next measurement starting at Step 3 | | | | |

Microdilution Assay in Clinical Patient Isolates

Broth Micro-Dilution Assay in Cation-Adjusted Mueller-Hinton (CA-MHB)

The assay protocol is adapted from the Clinical and Laboratory Standards Institute (CLSI) standardized method for broth microdilution. This methodology was used to evaluate the susceptibility of pathogenic clinical isolates towards different antibiotics in combination with a compound of the invention.

Antibiotic-resistant staphylococcal, enterococcal, enterobacterial or *acinetobacter* isolates were scraped from fresh Orientation Agar plates, suspended in saline solution with the turbidity adjusted to $OD_{610}$ of 0.1 (corresponds to 0.5 McFarland scale). Subsequently, the cultures were diluted 160× in CA-MHB medium and a volume of 80 µl was dispensed into each well of a 96 well microtiter plate. Plates were covered and incubated for 16 to 20 hours at 35° C. without shaking. Plates were then visually analyzed, scanned and subsequently the $OD_{610}$ was determined. Average and standard deviations were calculated from at least two wells with the same condition. Values were normalized to the DMSO control (which is 100%).

Results:

Correlation of the synergistic effect of compounds of the invention with tetracyclines on bacterial growth inhibition (% growth relative to DMSO; 4 µg/ml tetracyclines and 10 µg/ml compounds of the invention) and TetR/tetO interaction (% association of TetR to tetO relative to DMSO). Bacterial growth was analysed 16 to 20 hours after inoculation according to CLSI guidelines. $OD_{610}$ was determined with a Tecan Infinite F200 and normalized to the DMSO control. The interaction of TRIC compounds with the TetR protein and the effect on TetR-tetO operator DNA binding was analyzed with a FortéBio's Octet red and normalized to the DMSO control.

TABLE

| Compound Ex. No. | Growth (% rel. to DMSO) | Association (% rel. to DMSO) |
|---|---|---|
| 1 | 55.20 | 15.84 |
| 2 | 34.40 | 51.60 |
| 3 | 41.10 | 63.20 |
| 4 | 63.87 | |
| 5 | 56.57 | 30.49 |
| 6 | 60.43 | 25.61 |
| 7 | 56.50 | 26.83 |
| 8 | 69.68 | 42.57 |
| 9 | 25.91 | 16.22 |
| 10 | 47.14 | 25.68 |
| 11 | 26.14 | 19.59 |
| 12 | 5.76 | 1.60 |
| 13 | 4.74 | |
| 14 | 18.21 | 10.26 |
| 15 | 4.88 | 85.19 |
| 16 | 6.15 | 2.52 |
| 17 | 8.11 | 70.49 |
| 18 | 103.70 | 13.64 |
| 19 | 11.50 | 54.02 |
| 20 | 63.75 | 97.40 |
| 21 | 25.77 | |
| 22 | 61.29 | 108.99 |
| 23 | 8.15 | 22.69 |
| 24 | 48.15 | 54.12 |
| 25 | 90.15 | 11.76 |
| 26 | 55.92 | 43.52 |
| 27 | 58.69 | 23.15 |
| 28 | 46.79 | 36.62 |
| 29 | 23.58 | |
| 30 | 15.00 | 25.35 |
| 31 | 68.68 | 20.42 |
| 32 | 58.27 | 25.35 |
| 33 | 16.62 | 19.05 |
| 34 | 13.58 | 21.09 |
| 35 | 25.80 | 30.61 |
| 36 | 33.52 | 27.89 |
| 37 | 10.42 | 14.18 |
| 38 | 21.92 | 37.31 |

The invention claimed is:
1. A pharmaceutical composition comprising
   (a) one or more tetracyclines;
   (b) a TetR binding compound preventing TetR from dissociation of the tetO operator sequence in the presence of the inducing antibiotic tetracycline;

wherein the TetR binding compound (b) is a compound of formula

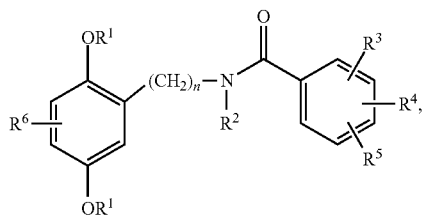

wherein
$R^1$ is hydrogen or methyl;
$R^2$ is hydrogen or methyl;
$R^3$, $R^4$ and $R^5$ are, independently of each other, hydrogen, lower alkyl, halo-lower alkyl, halogen, cyano, hydroxy, lower alkoxy, halo-lower alkoxy, phenoxy, amino, lower alkylamino, di-(lower alkyl)amino, optionally substituted lower alkylcarbonylamino, carboxy, lower alkylcarbonyl, lower alkoxycarbonyl, phenylcarbonyl, or phenyl;
$R^6$ is hydrogen, phenoxy or phenyl; and
n is 1, 2, 3 or 4.

2. A pharmaceutical composition according to claim 1, wherein the tetracycline (a) is selected from the group consisting of tetracycline, oxytetracycline, chlorotetracycline, demeclocycline, meclocycline, rolitetracycline, 6-thiatetracycline, 4-epi-anhydrochlortetracycline, aminomethylcycline, azatetracycline, fluorocycline, pentacycline, minocycline, doxycycline and tigecycline.

3. The pharmaceutical composition of claim 1, wherein the compound of formula (1) is:

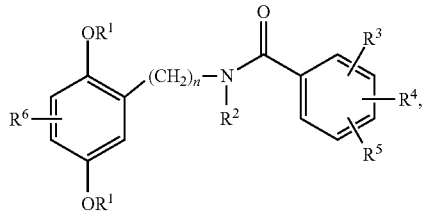

wherein
$R^1$ is hydrogen or methyl;
$R^2$ is hydrogen or methyl;
$R^3$ and $R^4$ are, independently of each other, hydrogen, lower alkyl, halo-lower alkyl, halogen, cyano, lower alkoxy, optionally substituted lower alkylcarbonylamino, or phenyl;
$R^5$ is hydrogen, methyl, trifluoromethyl, fluorine, chlorine or cyano;
$R^6$ is hydrogen, phenoxy or phenyl; and
n is 3 or 4, or n is 1, 2, 3 or 4 if $R^1$ is hydrogen.

4. The pharmaceutical composition of claim 1, wherein
$R^1$ is hydrogen;
$R^2$ is hydrogen or methyl;
$R^3$ and $R^4$ are, independently of each other, hydrogen, methyl, ethyl, propyl, isopropyl, isobutyl, tert-butyl, trifluoromethyl, 2,2,2-trifluoroethyl, fluorine, chlorine, bromine, cyano, methoxy, ethoxy, methoxymethylcarbonylamino, cyanomethylcarbonylamino, or tert-butylaminomethylcarbonylamino;
$R^5$ is hydrogen;
$R^6$ is hydrogen, phenoxy or phenyl; and
n is 1, 2, 3 or 4.

5. The pharmaceutical composition of claim 1, wherein
$R^1$ is hydrogen;
$R^2$ is hydrogen or methyl;
$R^3$ is hydrogen, methyl, ethyl, propyl, isopropyl, isobutyl, tert-butyl, trifluoromethyl, 2,2,2-trifluoroethyl, fluorine, chlorine, bromine, cyano, methoxy, ethoxy, methoxymethylcarbonylamino, cyanomethylcarbonylamino, or tert-butylaminomethylcarbonylamino;
$R^4$ is fluoro or trifluoromethyl;
$R^5$ is hydrogen;
$R^6$ is hydrogen, phenoxy or phenyl; and
n is 1, 2, 3 or 4.

6. A method of treatment of an infective bacterial disease comprising administering to a patient in need thereof an effective amount of a pharmaceutical composition according to claim 1.

7. A method of treatment of an infective bacterial disease comprising administering to a patient in need thereof an effective amount of a pharmaceutical composition according to claim 3.

8. a compound of formula (1),

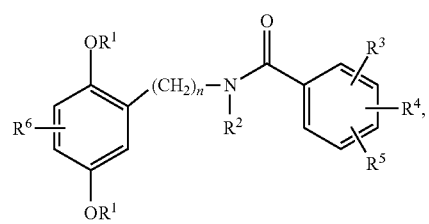

wherein
$R^1$ is hydrogen or methyl;
$R^2$ is hydrogen or methyl;
$R^3$ and $R^4$ are, independently of each other, hydrogen, lower alkyl, halo-lower alkyl, halogen, cyano, lower alkoxy, optionally substituted lower alkylcarbonylamino, or phenyl;
$R^5$ is hydrogen, methyl, trifluoromethyl, fluorine, chlorine or cyano;
$R^6$ is hydrogen, phenoxy or phenyl; and
n is 3 or 4, or n is 1, 2, 3 or 4 if $R^1$ is hydrogen.

9. The compound of claim 8, wherein
$R^1$ is hydrogen;
$R^2$ is hydrogen or methyl;
$R^3$ and $R^4$ are, independently of each other, hydrogen, methyl, ethyl, propyl, isopropyl, isobutyl, tert-butyl, trifluoromethyl, 2,2,2-trifluoroethyl, fluorine, chlorine, bromine, cyano, methoxy, ethoxy, methoxymethylcarbonylamino, cyanomethylcarbonylamino, or tert-butylaminomethylcarbonylamino;
$R^5$ is hydrogen;
$R^6$ is hydrogen, phenoxy or phenyl; and
n is 1, 2, 3 or 4.

10. The compound of claim 8, wherein $R^1$ is hydrogen;
$R^2$ is hydrogen or methyl;
$R^3$ is hydrogen, methyl, ethyl, propyl, isopropyl, isobutyl, tert-butyl, trifluoromethyl, 2,2,2-trifluoroethyl, fluorine, chlorine, bromine, cyano, methoxy, ethoxy, methoxymethylcarbonylamino, cyanomethylcarbonylamino, or tert-butylaminomethylcarbonylamino;
$R^4$ is fluoro or trifluoromethyl; $R^5$ is hydrogen;
$R^6$ is hydrogen, phenoxy or phenyl;
and n is 1, 2, 3 or 4.

* * * * *